(12) United States Patent
Yeung et al.

(10) Patent No.: US 10,065,323 B2
(45) Date of Patent: Sep. 4, 2018

(54) MAGNETIC-ANCHORED ROBOTIC SYSTEM

(71) Applicant: Bio-Medical Engineering (HK) Limited, Hong Kong (HK)

(72) Inventors: Chung Kwong Yeung, Hong Kong (HK); Kai Leung Yung, Hong Kong (HK)

(73) Assignee: Bio-Medical Engineering (HK) Limited, Hong Kong (HK)

( * ) Notice: Subject to any disclaimer, the term of this patent is extended or adjusted under 35 U.S.C. 154(b) by 0 days.

(21) Appl. No.: 13/871,915

(22) Filed: Apr. 26, 2013

(65) Prior Publication Data
US 2013/0289581 A1    Oct. 31, 2013

Related U.S. Application Data

(60) Provisional application No. 61/638,828, filed on Apr. 26, 2012, provisional application No. 61/718,252, filed on Oct. 25, 2012.

(51) Int. Cl.
*A61B 17/00* (2006.01)
*B25J 13/08* (2006.01)
(Continued)

(52) U.S. Cl.
CPC ............ *B25J 13/088* (2013.01); *A61B 17/00* (2013.01); *A61B 17/00234* (2013.01);
(Continued)

(58) Field of Classification Search
CPC ... B25J 9/042; B25J 9/046; B25J 9/104; B25J 117/0266; A61B 19/203; A61B 19/22;
(Continued)

(56) References Cited

U.S. PATENT DOCUMENTS

| | | | |
|---|---|---|---|
| 4,278,077 A | 7/1981 | Mizumoto | |
| 5,604,531 A | 2/1997 | Iddan et al. | |

(Continued)

FOREIGN PATENT DOCUMENTS

| | | |
|---|---|---|
| CN | 101091665 | 12/2007 |
| JP | 2004321692 | 11/2004 |

(Continued)

OTHER PUBLICATIONS

Definitin of Secure. Merriam-Webster Dictionary, retrieved on Sep. 12, 2016; Retrived from the Internet: <http://www.merriam-webster.com/dictionary/secure>.*

(Continued)

*Primary Examiner* — William Thomson
*Assistant Examiner* — Sebastian X Lukjan
(74) *Attorney, Agent, or Firm* — Baker & McKenzie, LLP

(57) ABSTRACT

A robotic actuator includes an internal anchor and an instrument. The internal anchor is adapted to be inserted into a body via an entrance port, positioned inside the body, and magnetically coupled with an external anchor positioned outside the body. The instrument is adapted to be inserted into the body via the entrance port and secured to the internal anchor. The instrument includes an end-effector having multiple degrees of movement via multiple axes, and a plurality of actuators that provide the multiple degrees of movement.

30 Claims, 27 Drawing Sheets

(51) Int. Cl.
*A61B 34/00* (2016.01)
*A61B 17/34* (2006.01)
*A61B 34/30* (2016.01)
*A61B 90/00* (2016.01)

(52) U.S. Cl.
CPC .......... *A61B 17/3417* (2013.01); *A61B 34/30* (2016.02); *A61B 34/73* (2016.02); *A61B 34/76* (2016.02); *A61B 17/3423* (2013.01); *A61B 2017/00283* (2013.01); *A61B 2017/00876* (2013.01); *A61B 2017/3484* (2013.01); *A61B 2034/302* (2016.02); *A61B 2090/371* (2016.02); *Y10S 901/09* (2013.01); *Y10S 901/34* (2013.01); *Y10S 901/41* (2013.01); *Y10T 428/13* (2015.01)

(58) Field of Classification Search
CPC .............. A61B 19/201; A61B 19/2203; A61B 2019/2242
USPC ........................... 606/1; 700/258; 901/15, 19
See application file for complete search history.

(56) References Cited

U.S. PATENT DOCUMENTS

| | | | |
|---|---|---|---|
| 6,240,312 B1 | 5/2001 | Alfano et al. | |
| 6,402,686 B1 | 6/2002 | Ouchi | |
| 6,442,435 B2* | 8/2002 | King et al. | 607/117 |
| 6,648,814 B2 | 11/2003 | Kim et al. | |
| 6,676,684 B1* | 1/2004 | Morley | A61B 19/2203 |
| | | | 606/205 |
| 6,702,734 B2 | 3/2004 | Kim et al. | |
| 6,719,684 B2 | 4/2004 | Kim et al. | |
| 6,776,165 B2 | 8/2004 | Jin | |
| 6,936,003 B2 | 8/2005 | Iddan | |
| 6,984,205 B2 | 1/2006 | Gazdzinski | |
| 6,991,627 B2 | 1/2006 | Madhani et al. | |
| 7,039,453 B2 | 5/2006 | Mullick et al. | |
| 7,042,184 B2 | 5/2006 | Oleynikov et al. | |
| 7,066,879 B2 | 6/2006 | Fowler et al. | |
| 7,111,769 B2* | 9/2006 | Wales et al. | 227/178.1 |
| 7,126,303 B2 | 10/2006 | Farritor et al. | |
| 7,169,104 B2 | 1/2007 | Ueda et al. | |
| 7,182,089 B2 | 2/2007 | Ries | |
| 7,199,545 B2 | 4/2007 | Oleynikov et al. | |
| 7,311,107 B2 | 12/2007 | Harel et al. | |
| 7,339,341 B2 | 3/2008 | Oleynikov et al. | |
| 7,429,259 B2 | 9/2008 | Cadeddu et al. | |
| 7,492,116 B2 | 2/2009 | Oleynikov et al. | |
| 7,625,338 B2 | 12/2009 | Gilad et al. | |
| 7,691,103 B2 | 4/2010 | Fernandez et al. | |
| 8,145,295 B2 | 3/2012 | Boyden et al. | |
| 8,343,171 B2 | 1/2013 | Farritor et al. | |
| 2002/0103417 A1 | 8/2002 | Gazdzinski | |
| 2003/0020810 A1 | 1/2003 | Takizawa et al. | |
| 2003/0092964 A1 | 5/2003 | Kim et al. | |
| 2003/0114731 A1 | 6/2003 | Cadeddu et al. | |
| 2003/0167000 A1 | 9/2003 | Mullick et al. | |
| 2004/0050395 A1 | 3/2004 | Ueda et al. | |
| 2004/0176664 A1 | 9/2004 | Iddan | |
| 2005/0029978 A1 | 2/2005 | Oleynikov | |
| 2005/0096502 A1 | 5/2005 | Khalili | |
| 2005/0165449 A1 | 7/2005 | Cadeddu et al. | |
| 2005/0273139 A1 | 12/2005 | Krauss et al. | |
| 2005/0288555 A1 | 12/2005 | Binmoeller | |
| 2006/0079897 A1* | 4/2006 | Harrison et al. | 606/61 |
| 2006/0119304 A1 | 6/2006 | Farritor et al. | |
| 2006/0149135 A1 | 7/2006 | Paz | |
| 2006/0196301 A1 | 9/2006 | Oleynikov et al. | |
| 2006/0198619 A1 | 9/2006 | Oleynikov et al. | |
| 2007/0032701 A1 | 2/2007 | Fowler | |
| 2007/0080658 A1 | 4/2007 | Farritor et al. | |
| 2007/0123748 A1 | 5/2007 | Meglan | |
| 2007/0157937 A1 | 7/2007 | Takayasu et al. | |
| 2007/0241714 A1 | 10/2007 | Okeynikov et al. | |
| 2007/0255273 A1 | 11/2007 | Fernandez et al. | |
| 2008/0004634 A1 | 1/2008 | Farritor et al. | |
| 2008/0058835 A1 | 3/2008 | Farritor et al. | |
| 2008/0058989 A1 | 3/2008 | Oleynikov et al. | |
| 2008/0111513 A1 | 5/2008 | Farritor et al. | |
| 2008/0221591 A1 | 9/2008 | Farritor et al. | |
| 2008/0249359 A1 | 10/2008 | Abraham-Fuchs et al. | |
| 2008/0269779 A1* | 10/2008 | Cadeddu et al. | 606/130 |
| 2009/0024142 A1* | 1/2009 | Ruiz Morales | B25J 9/041 |
| | | | 606/130 |
| 2009/0043246 A1* | 2/2009 | Dominguez | 604/21 |
| 2009/0048612 A1 | 2/2009 | Farritor et al. | |
| 2009/0054909 A1* | 2/2009 | Farritor et al. | 606/130 |
| 2009/0069821 A1 | 3/2009 | Farritor et al. | |
| 2009/0171354 A1* | 7/2009 | Deville et al. | 606/51 |
| 2009/0171373 A1 | 7/2009 | Farritor et al. | |
| 2009/0259340 A1 | 10/2009 | Umemoto et al. | |
| 2010/0160739 A1* | 6/2010 | Van Lue | 600/210 |
| 2010/0194707 A1* | 8/2010 | Hotelling et al. | 345/173 |
| 2010/0256636 A1 | 10/2010 | Fernandez et al. | |
| 2010/0318059 A1 | 12/2010 | Farritor et al. | |
| 2011/0087223 A1 | 4/2011 | Spivey | |
| 2011/0087224 A1 | 4/2011 | Cadeddu et al. | |
| 2011/0224605 A1 | 9/2011 | Farritor et al. | |
| 2011/0237890 A1 | 9/2011 | Farritor et al. | |
| 2011/0283822 A1 | 11/2011 | Cadeddu et al. | |
| 2011/0284014 A1 | 11/2011 | Cadeddu et al. | |
| 2011/0285488 A1 | 11/2011 | Scott et al. | |
| 2011/0313415 A1 | 12/2011 | Fernandez et al. | |
| 2012/0035416 A1 | 2/2012 | Fernandez et al. | |
| 2012/0065627 A1 | 3/2012 | Ghabrial et al. | |
| 2012/0179168 A1 | 7/2012 | Farritor et al. | |
| 2013/0012821 A1* | 1/2013 | Lin et al. | 600/473 |
| 2013/0041360 A1 | 2/2013 | Farritor et al. | |

FOREIGN PATENT DOCUMENTS

| | | |
|---|---|---|
| JP | 2005028006 | 2/2005 |
| WO | 2007149559 | 12/2007 |
| WO | 2008103212 | 8/2008 |
| WO | 2009014917 | 1/2009 |
| WO | 2009023851 | 2/2009 |
| WO | 2010083480 | 7/2010 |
| WO | 2011044468 | 4/2011 |
| WO | 2011075693 | 6/2011 |
| WO | 2012035157 | 3/2012 |
| WO | WO 2012164517 A1 * | 12/2012 |

OTHER PUBLICATIONS

International Search Report and Written Opinion issued in PCT/CN2013/000478 dated Jul. 25, 2013, nine pages.
International Search Report and Written Opinion issued in PCT/CN2013/000480 dated Aug. 8, 2013, eleven pages.

* cited by examiner

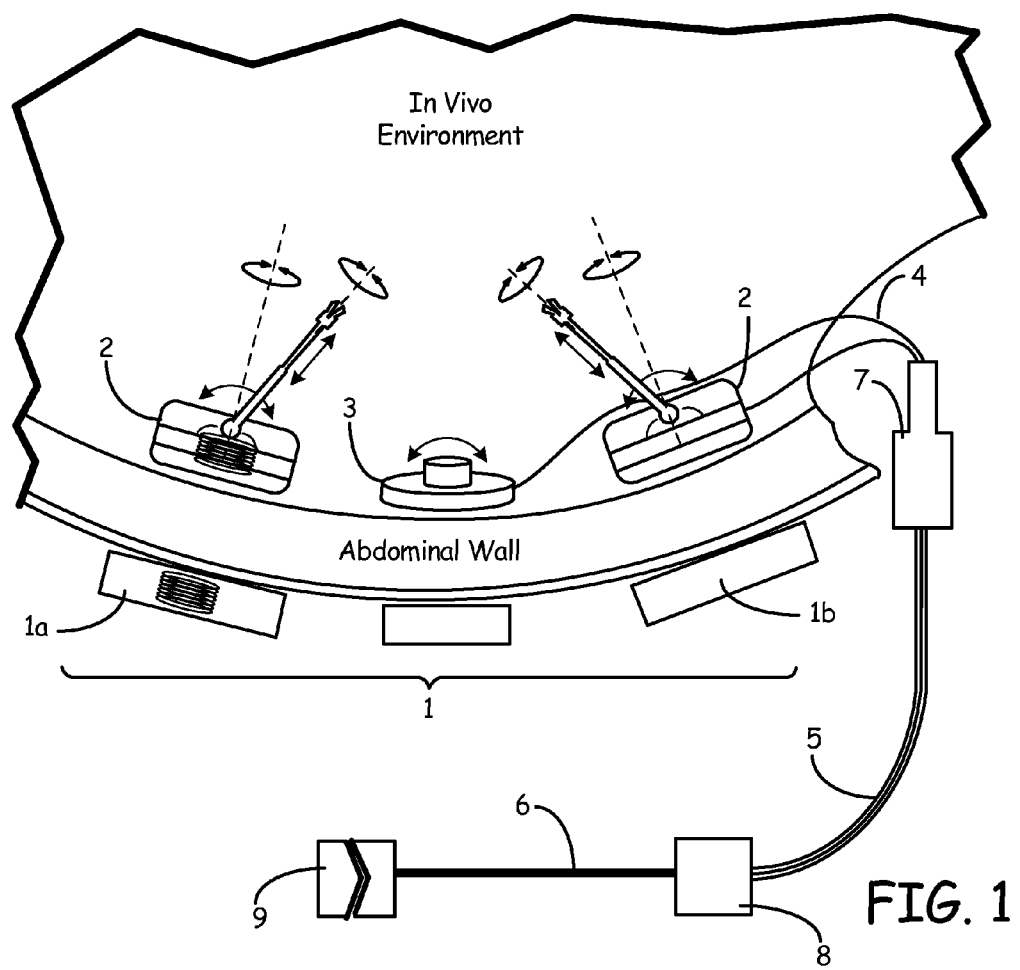
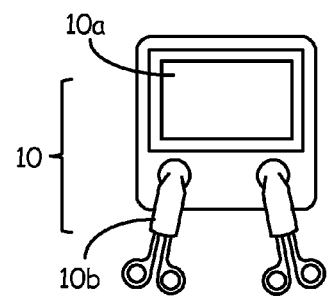 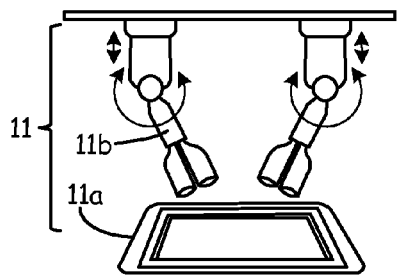
FIG. 1
FIG. 1A　　　FIG. 1B

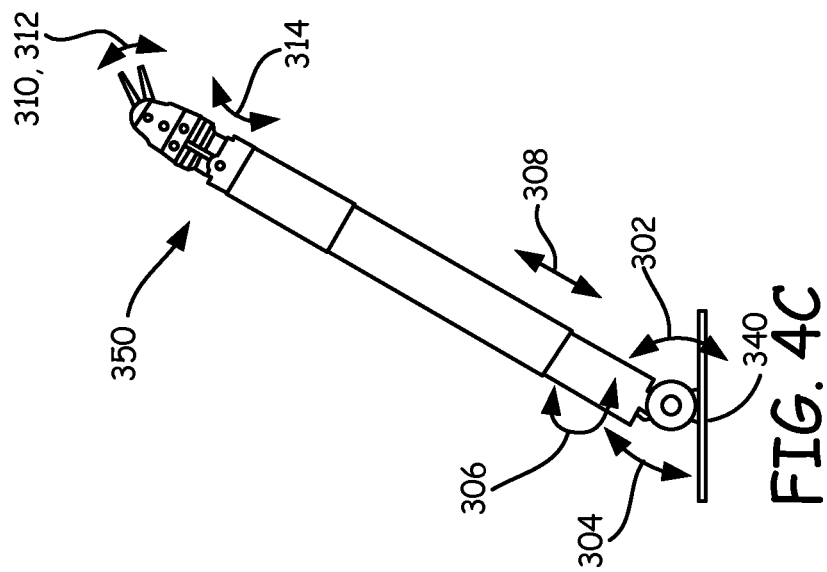
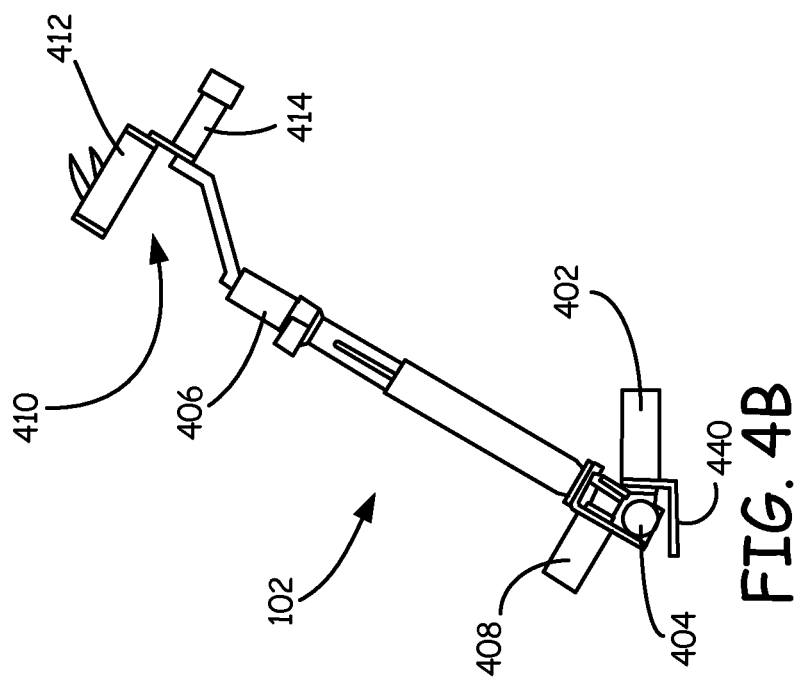

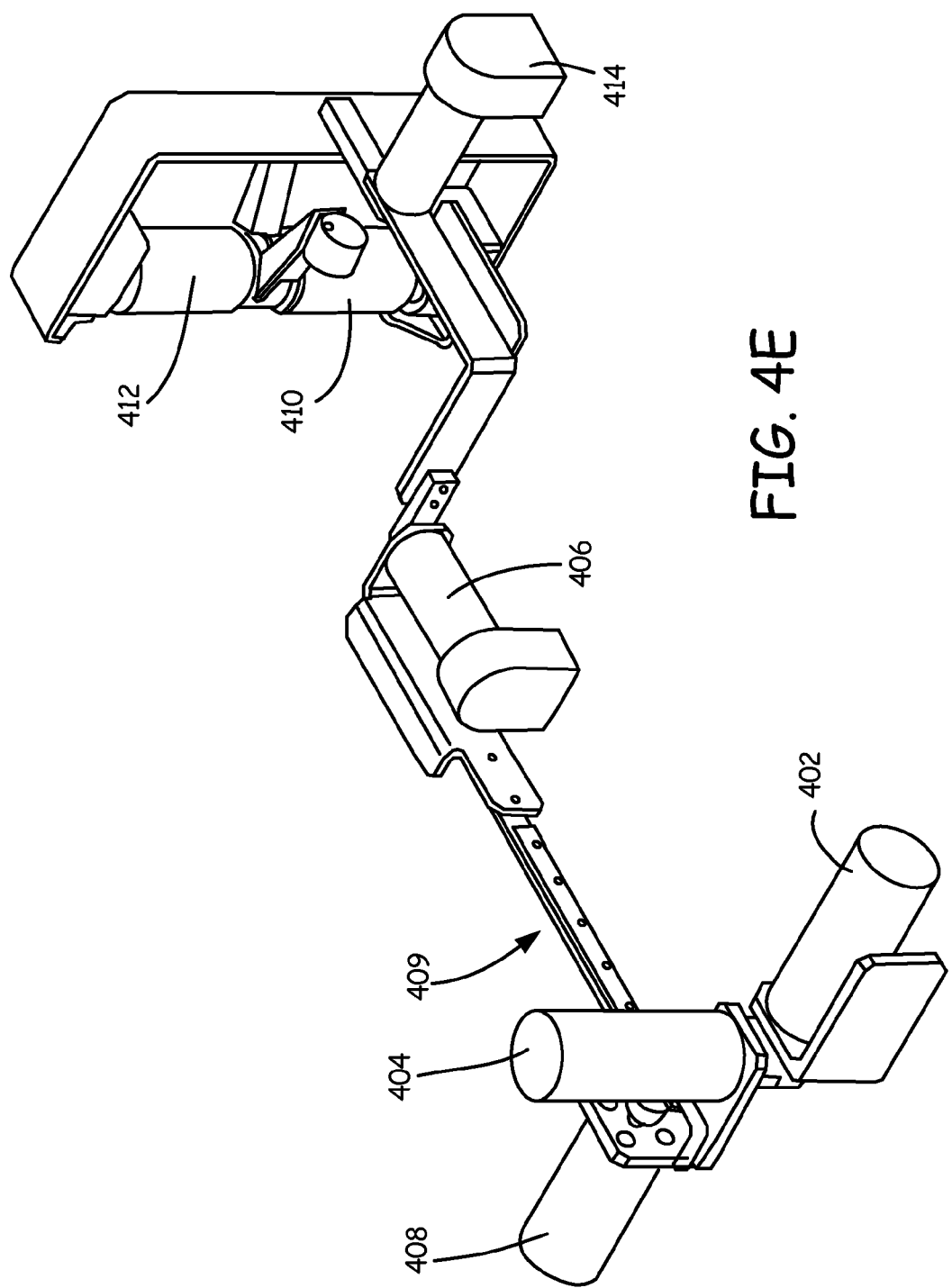

MAGNETIC-ANCHORED ROBOTIC SYSTEM

CROSS-REFERENCE TO RELATED APPLICATIONS

This application claims priority to U.S. Provisional App. Ser. No. 61/638,828, filed Apr. 26, 2012 and U.S. Provisional App. Ser. No. 61/718,252, filed Oct. 25, 2012, each of which is hereby incorporated by reference in its entirety. This application is related to U.S. application Ser. No. 13/835,653, filed Mar. 15, 2013, U.S. application Ser. No. 13/835,680, filed Mar. 15, 2013, and U.S. application Ser. No. 13/871,296, filed Apr. 26, 2013, now U.S. Pat. No. 9,020,640, each of which is hereby incorporated by reference in its entirety.

BACKGROUND

Surgeons have traditionally depended on external illumination from the operating room light and adequate exposure to obtain a good surgical view. This often requires large incisions, especially if the surgeon has larger hands, to provide access for the operation. The introduction of fiber optics in modern endoscopes has allowed surgeons to see clearly with good illumination inside a bodily cavity without having to make a big incision. Minimally Invasive Surgery (MIS) has now replaced most conventional open surgical operations. Computer-assisted or robotic technology has contributed further to the development of MIS as the computer sensors of the robotic machine can reliably and delicately translate the movements of the surgeon's fingers and wrists into movements of the slave laparoscopic instruments inside the body cavities. These developments have allowed good dexterity and precision control of surgical instruments for fine reconstructive surgery in a small confined space.

However, the MIS approach requires multiple incisions for the insertion of the camera and various laparoscopic instruments. Over the past few years, Laparo-Endoscopic Single-Site (LESS) surgery technologies have become available, but these suffer immensely from a lack of proper triangulation between the camera and the working instruments, which is important for good operative ergonomics and hence ease and success of surgery.

Natural orifice translumenal endoscopic surgery (NOTES) is an alternative to open abdominal surgery that uses endoscopic techniques with a view to completely avoid the need for external abdominal wall incisions. Theoretically, NOTES offers advantages by minimizing access trauma and the various complications associated with external incisions including wound infections, pain, hernia formation, unsightly abdominal scars and adhesions.

However, the NOTES approach suffers from significant drawbacks including inadequacy of proper triangulation of surgical instruments and hence poor working ergonomics, an inability to apply off-axis forces, and difficulties in passing multiple instruments into the abdominal cavity for proper surgical manipulations.

BRIEF SUMMARY

In an embodiment, a robotic actuator includes an internal anchor and an instrument. The internal anchor is adapted to be inserted into a body via an entrance port, positioned inside the body, and magnetically coupled with an external anchor positioned outside the body. The instrument is adapted to be inserted into the body via the entrance port and secured to the internal anchor. The instrument includes an end-effector having multiple degrees of movement via multiple axes, and a plurality of actuators that provide the multiple degrees of movement.

BRIEF DESCRIPTION OF THE DRAWINGS

FIG. 1 is a general schematic view of an exemplary surgical robotic system.

FIGS. 1A and 1B are front views of exemplary human-machine interfaces.

FIG. 4B is a side view of an exemplary surgeon manipulator.

FIG. 4C is a side view of an exemplary micro robotic manipulator.

FIG. 4E is a perspective view of the exemplary surgeon manipulator of FIG. 4D in an extended position.

DETAILED DESCRIPTION

A Magnetic-anchored Robotic System (MRS) allows computer-assisted minimally-invasive surgery using multiple independent in-vivo miniature robots that can have a full seven-degrees of freedom of movement in different axis (note that in addition to the degrees of freedom of movement of the miniature robots discussed below, two more degrees of freedom are available by translating the miniature robots along the abdominal wall). Intra-abdominal operations can be performed under the surveillance of an in-vivo swivel camera under remote control by the surgeon through an external computer console. Each of the miniature robotic instruments, camera and other devices may be inserted into the abdominal cavity via either a single incision (for example, through the umbilicus) or through a natural orifice and may be secured into position by an external electro-magnetic anchoring and positioning device outside the abdominal wall at selected sites to provide operative ergonomics and triangulation between camera and instruments. The control of such miniature robotic system inside the abdominal cavity can be, for example, via a wired or a hybrid combination of wired and wireless communications, depending on the situation and the condition of the patient. In some arrangements, power will be transmitted to the miniature robotic instruments (effectors), by a pair of conductors, while the control signals of the same can be transmitted by wire or wirelessly.

The camera as well as all laparoscopic instruments can be inserted into the abdominal cavity through a single incision or through a natural orifice. The laparoscopic instruments can then be anchored and positioned through an external electro-magnet placed outside the abdominal wall. MRS can therefore allow MIS to be performed with the benefits of both computer-assisted or robotic surgery, as well as using either only a single incision or through a natural orifice. An exemplary MRS may include:

(i) one or more externally-mounted electro-magnetic anchoring and positioning devices;

(ii) multiple internal electro-magnetic anchoring devices, each fitted with an independent miniature robotic surgical instrument capable of, for example, seven-degrees freedom of movements via multiple axis; and (iii) a surgeon's computer console that provides surgical control and manipulation.

Thus, exemplary advantages including minimized access trauma, provision of unrestricted or less restricted and more dexterous movement of instruments inside the cavity and enabling proper or improved triangulation of instruments for optimal or improved operative ergonomics can be achieved.

Figure 23:
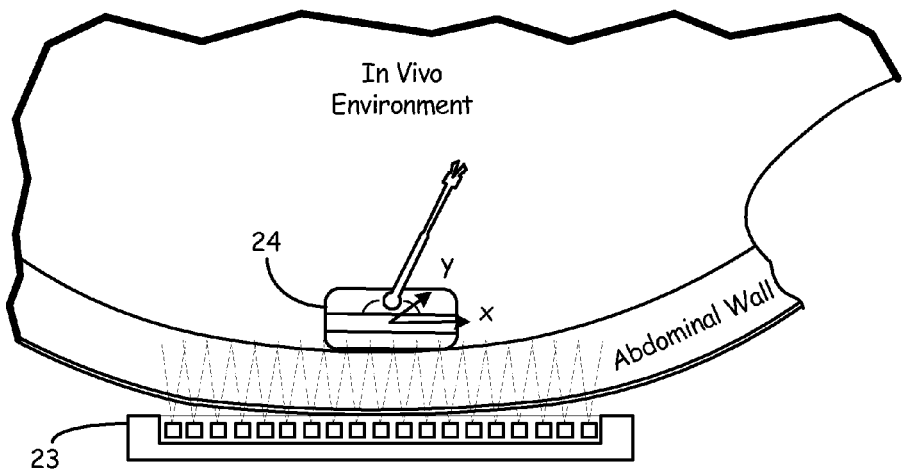
FIG. 23 is a side view of an exemplary micro robotic manipulator in an in vivo environment.
Figure 24A:
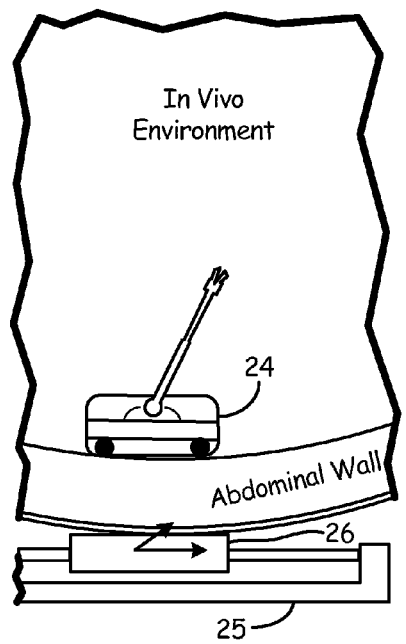
FIGS. 24A and 24B are side views of an exemplary micro robotic manipulator in an in vivo environment.
Figure 24B:
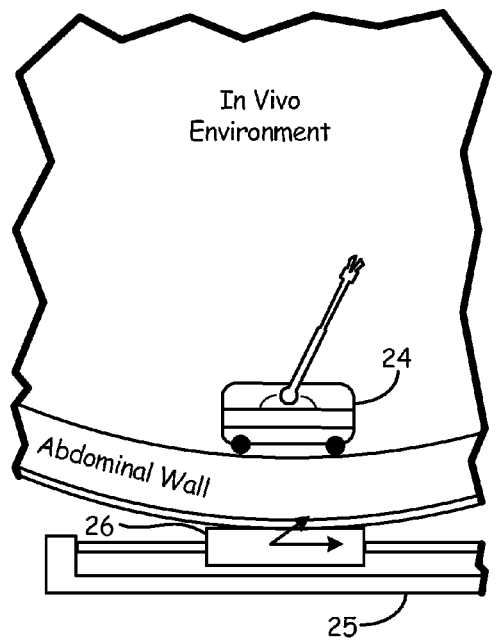

Referring to FIG. 1, the system may include one or more magnetic or electromagnetic location fixing device(s) 1 (hereafter collectively referred to as the electromagnetic location fixing device 1, which includes examples including permanent/non-electric magnets unless otherwise specifically excluded) placed on the outer abdominal wall associated with remotely controlled robotic manipulator(s) 2 inside the body. The electromagnetic location fixing device 1 may include a servo mechanism that is remotely controlled to control the position of the internal electromagnetic anchoring device. The robotic manipulator inside the human body can therefore be moved and be positioned by an externally supplied magnetic field interacting with one or more permanent magnets or electromagnets included in the electromagnetic location fixing device 1 together with the internal electromagnetic anchoring device. Such an externally supplied magnetic field may be moved by a X-Y servo mechanism to a designated position thus relocating the robotic arm 24 to the designated position and then refix again as shown in FIG. 24. As another example, the electromagnetic location fixing device 23 shown in FIG. 23 may be in the form of a linear induction stator on the outside of the abdominal wall such that when an alternating current of appropriate frequency is applied to the stator on the outside of the abdominal wall, the inside flap 24 will levitate and move forward. When such an alternating current is applied in pulse form, the inside flap 24 will move forward in small steps. Such control may also be provided by a control computer.

For illustrative purposes, each location fixing device is shown with one robotic manipulator; however, there may be multiple robotic manipulators for one location fixing device or multiple location fixing devices for one robotic manipulator. For example, each device may detect the current position of the end effector of the corresponding multi-axis micro robotic manipulator 2 inside the human body. The multi-axis micro robotic manipulator 2 inside the body may detect the current position of the end effector. The micro robotic manipulator 2 may include various end effectors such as a gripping device 16 (for example, as shown in FIG. 6) and an imaging device 3 for performing a given treatment and visualizing the in vivo environment respectively.

The manipulator 2 can be folded and inserted into the body cavity through an entrance port 7 in the form of a hollow cylinder mounted on a minimal invasive opening or the like of the patient. It may be connected to a flexible cable 4 passing through the entrance port 7 and linked to a central control computer 8 via an electrical wire 5 or wirelessly. The entrance port 7 is in the range of 1.5-2 cm in diameter in some examples but may vary. The range of 1.5-2 cm is advantageous as it is big enough for equipment (manipulators, etc) to pass through and small enough to be accommodated by most natural orifices.

Figure 2A:
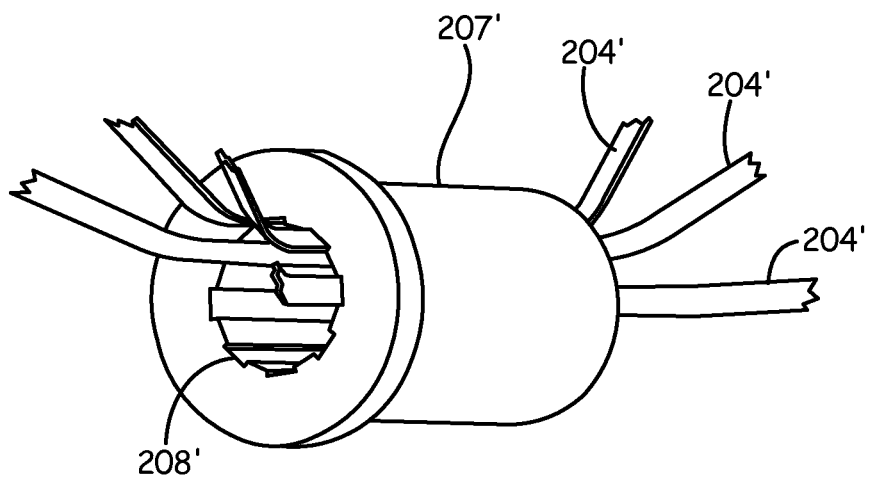
FIGS. 2A and 2B are perspective views of exemplary entrance ports.
Figure 2B:
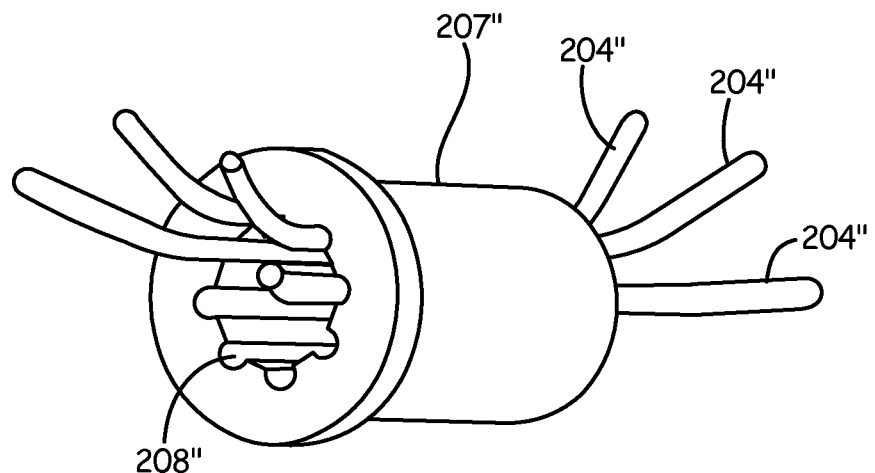

Referring to FIGS. 2A and 2B, the entrance ports 207' and 207" may be shaped to accommodate flexible cables 204' and 204" in a manner that permits multiple of the manipulators 2 to be inserted through the same single entrance port 207. An inner wall of the entrance ports 207' and 207" includes207" includes one or more recesses of a shape complementary to the wires 204' and 204".

In the example shown in FIG. 2A, the recesses 208' in the inner wall of the entrance port 207' are slot shaped and include a flat surface to accommodate the flat cable 204'. In some examples, a cross section of the inner wall may be in the shape of a polyhedron having the recesses 208' immediately joining an adjacent recess 208'. In other examples, the recesses 208' may be distributed circumferentially about the inner surface of the entrance port 207'. The recesses 208' may be distributed equally or unequally about the inner surface of the entrance port 207'.

In the example shown in FIG. 2B, the recesses 208" in the inner wall of the entrance port 207" are rounded to accommodate the round cable 204". In some examples, the recesses 208" immediately join an adjacent recess 208". In other examples, the recesses 208" may be distributed circumferentially about the inner surface of the entrance port 207". The recesses 208" may be distributed equally or unequally about the inner surface of the entrance port 207".

It will be appreciated that the above described shapes are exemplary in nature and can be selected from a variety of other shapes according to a particular implementation. Providing the recesses 208 allows for the use of the same entrance port for many of the manipulators 2 by clearing the opening of the entrance port 207 of the cables 204 to allow passage of another manipulator 2. In this way, trauma associated with the insertion of entrance ports, trocars, etc, can be minimized by reusing the same single entrance port for several or all of the manipulators 2.

Depending on the application, the signal transmission between the remotely controlled micro robotic manipulator 2 and the central control computer 8 can be performed through a wired connection (for example, via the entrance port 7 over a conductive cable or an optical cable) or a wireless connection (for example, via inductive coupling with a pickup coil incorporated in the location fixing device as shown in device 1a). Power for the manipulator 2 may also be supplied via the location fixing device 1 wirelessly through the abdominal wall. A hybrid such as a wired power supply and wireless control signal may also be used.

Also, in cases where the electromagnetic location fixing device 1 is controllable by the central control computer 8, a wired or wireless connection may be provided from the central control computer 8 to the electromagnetic location fixing device 1. Alternatively, or in addition, electromagnetic location fixing device 1 may communicate wirelessly with the micro robotic manipulator 2, which is connected to the central control computer 8 through a wired connection, for example via the entrance port 7, to provide communication between the electromagnetic location fixing device 1 and the central control computer 8. The central control computer 8 may control positioning servos of the electromagnetic location fixing device 1 as well as activating/deactivating a fixing control. The fixing control may be, for example, activating an electromagnet in the electromagnetic fixing device 1. The fixing control is not necessarily a discrete on/off control and may also be variable.

The central control computer 8 can adjust the positions and actions of the manipulators 2 independently of each other by the corresponding movement of the trigger unit 10b, 11b controlled by an operator through a human machine interface 9 connecting to the controller via a cable 6. The interface 9 may include a display screen 10a, 11a and a pair of trigger units 10b, 11b, which may be different types such as the remote operation type 10 shown in FIG. 1A and multi-axis end-effector simulator type 11 shown in FIG. 1B. In the multi-axis end-effector simulator type 11, the trigger unit 11b has a multi-axis robotic joint that can provide fine position control of the end effector of the manipulator 2 with several degrees of freedom. The movement control can also include force feedback.

Also, the number of inserted miniature robots is not limited to the number that can be controlled by one operator through the human machine interface 9. A second human machine interface may be provided for an assistant operator to also control miniature robots if needed for the operation.

Figure 3:
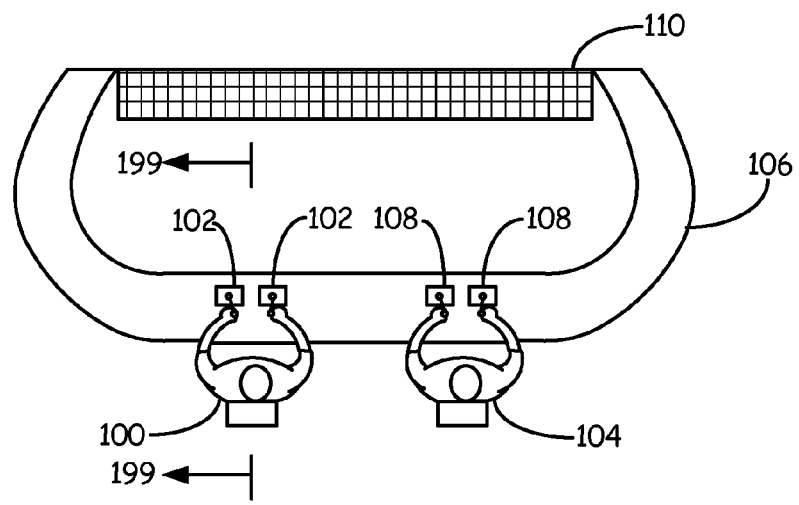
FIG. 3 is a perspective view of an exemplary surgeon console.

Referring to FIG. 3, a main surgeon 100 controls a pair of controls 102 while an assistant 104 working on the same surgeon console 106 or another surgeon console controls additional controls 108. The main surgeon 100 and/or the assistant 104 may also control various cameras. The main surgeon 100 and the assistant 104 can view the same display 110 or they may view separate displays, for example, showing different views of the patient. The display 110 may be a 2D display, a 3D display, a naked eye 3D display, or other type of suitable display. The assistant 104 may simultaneously operate and assist in the operation. Two or more operators may advantageously work on the same patient at the same time while maintaining dialog with each other. It will be appreciated that while a main surgeon and an assistant surgeon have been described, the console 106 may be operated by any one or two (or more) operators generically.

Figure 4A:
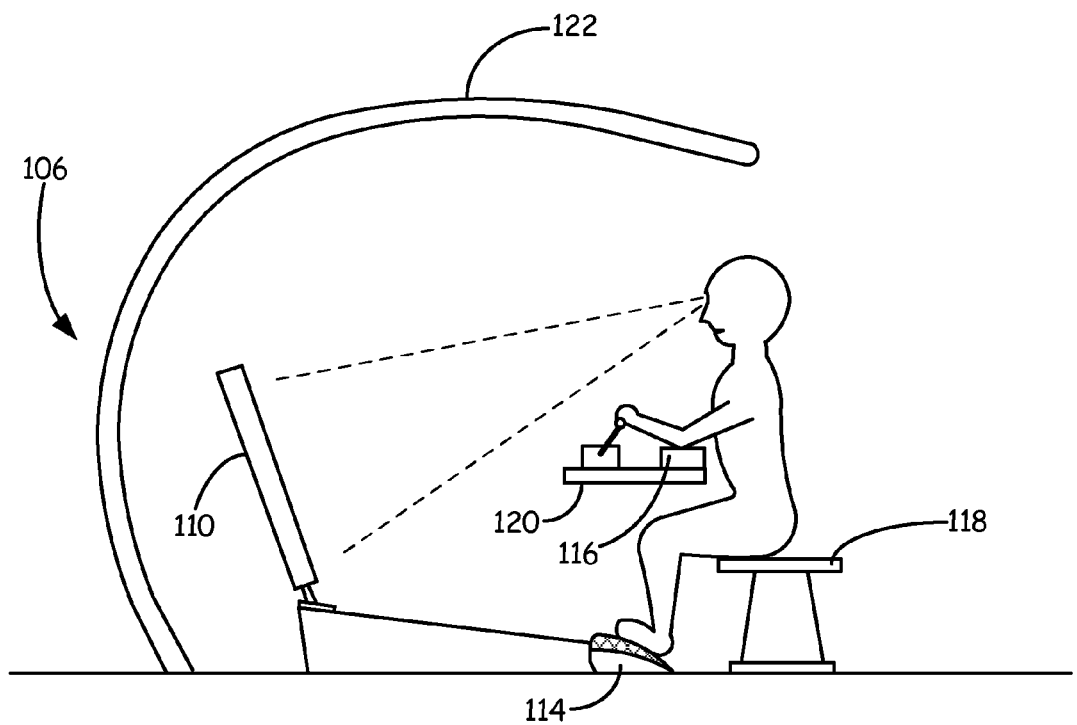
FIG. 4A is a side view of an exemplary surgeon console.
Figure 4D:
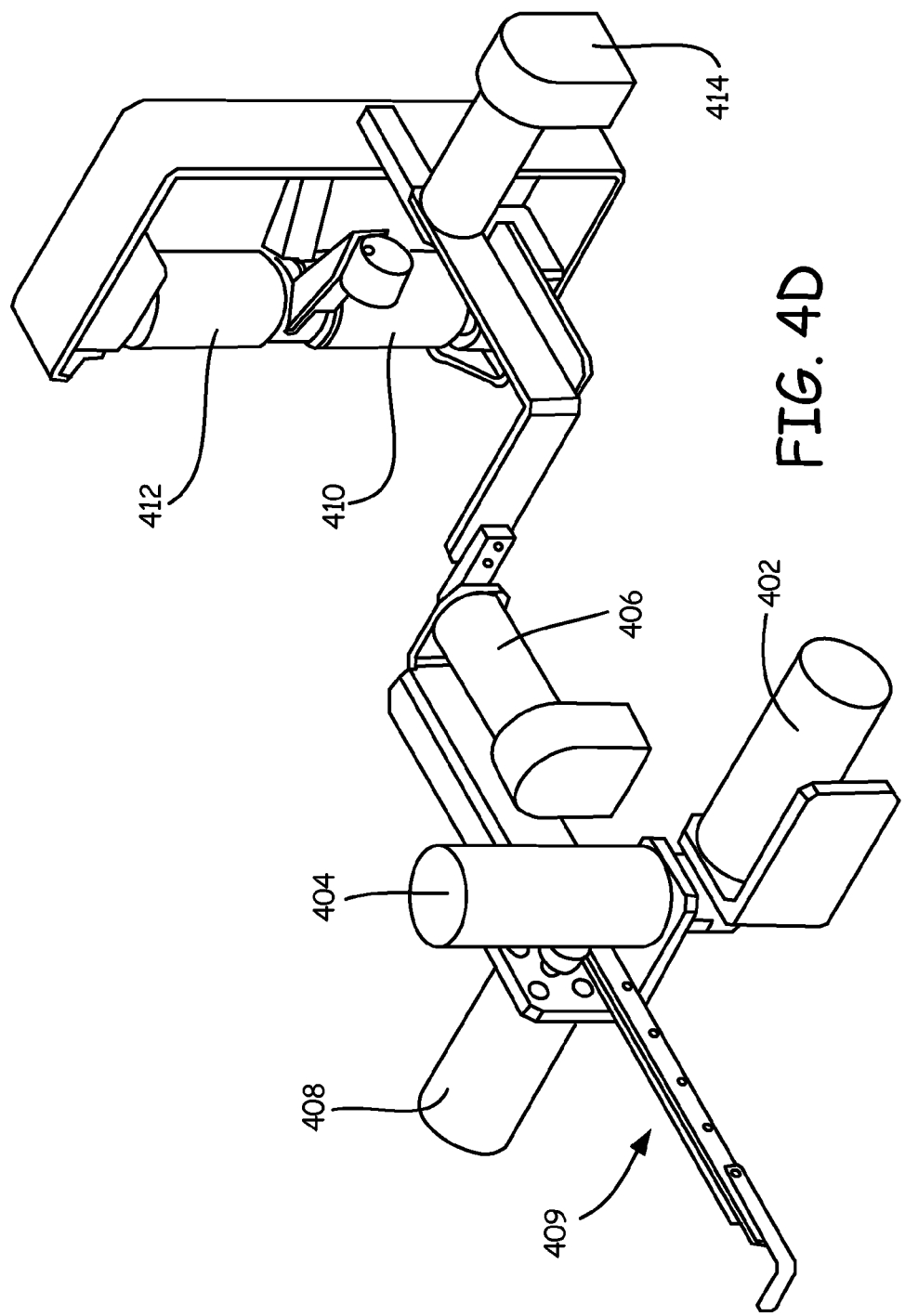
FIG. 4D is a perspective view of an exemplary surgeon manipulator.
Figure 4F:
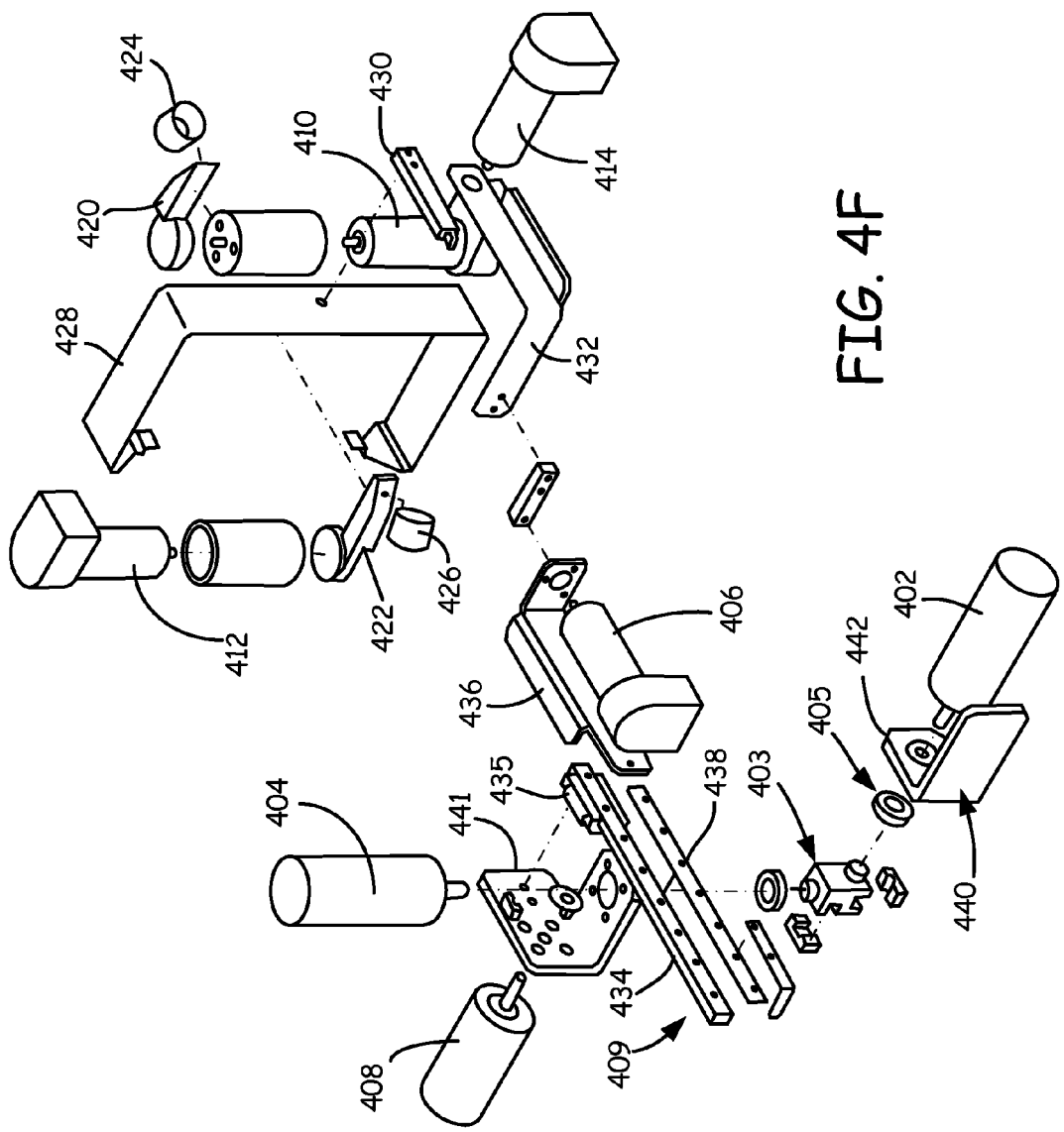
FIG. 4F is an exploded view of the exemplary surgeon manipulator of FIG. 4D.

Referring to FIGS. 3 and 4A, the surgeon console 106 may be ergonomically arranged including one or more of the foot rest 114, the arm rest 116 and the seat 118. The foot rest 114 may incorporate switches to switch the controls 102 (and/or the controls 108) to control the camera instead of the manipulators/robots or vice-versa. The foot rest 114 may also incorporate controls to control manual focusing of the camera(s). The foot rest 114, arm rest 116, controls 102, controls 108 and/or any combination thereof may include sensor/actuators to detect the presence of the operator in order to enable/disable the robotic system.

The surgeon console 106 may also be arranged to avoid light reflection. For example, the display 110 may be positioned such that at least a portion is below a height of the table 120 at which the surgeon sits. The display 110 may also be angled such that reflections are not passed or reduced to the viewer at the table 120. The light shelter 122 may also be provided to reduce ambient lighting that may could cause reflections.

Haptic feedback may be provided to the main surgeon 100 and/or the assistant 104. A resisting force may be measured by the in-vivo robotic manipulator 2, for example via an onboard sensor such as a load cell. The resisting force may also be estimated from an amount of energy (e.g., voltage, current or power) used by the manipulator 2. Force feedback based on the resisting force may be provided to the main surgeon 100 and/or the assistant 104 via the manipulators 102 and 108 respectively.

For example, with reference to FIGS. 4B and 4D-4F, a surgeon's manipulator 102 may include motor/encoders 402, 404, 406, 408, 410, 412 and 414. The motor/encoder 402 may detect and provide haptic feedback for pitch. For example, the motor/encoder 402 may be coupled to a joint element 403 with a bushing/washer 405 there between. Thus, the motor/encoder can detect rotation with respect to the joint element 403 and provide haptic feedback to this axis of movement. The motor/encoder 404 may detect and provide haptic feedback for sway. The motor/encoder 406 may detect and provide haptic feedback for wrist yaw. The motor/encoder 408 may detect and provide haptic feedback for extension/retraction. For example, the motor/encoder 408 may be coupled to the linear guide rail 409. As the linear guide rail is extended/retracted by the surgeon/operator, the motor/encoder 408 is rotated. Thus, the motor/encoder 408 can detect extension/retraction and provide haptic feedback to this axis of movement. The motor/encoders 410 and 412 may detect and provide haptic feedback for gripping. The motor/encoder 414 may detect and provide haptic feedback for wrist pitch. The motor/encoders 404, 406, 410, 412 are arranged in a manner similar to described above with respect to the motor/encoder 402.

Manipulator ends 420, 422 correspond with manipulator ends of a robotic actuator. The manipulator ends 420, 422 include contact portions 424, 426 (e.g., cylinders), to provide opposing surfaces by which movement of the manipulator ends by the surgeon in various directions is facilitated. The manipulators 420, 422 are respectively coupled to the motor/encoders 410, 412. The manipulators 420, 422 may be positioned adjacent to each other with the motor/encoders 410, 412 extending away from the manipulators 420, 422 in different (in some cases opposite) directions. Opposing ends of the motor/encoders 410, 412 may be secured to a frame 428, which may be C shaped.

The frame 428 may be secured to the motor encoder 414 via a frame member 430. The frame member 430 may be secured to the frame 428 at a central point of the frame 428 such that a rotational axis is centered. The motor/encoder 414 may also be coupled to a frame member 432. Thus, the motor/encoder 414 may detect rotational movement of the frame member 430 with respect to the frame member 432 thereby detecting rotational movement of the entire assembly including the manipulator ends 420, 422 and the motor/encoders 410 and 412.

The frame member 432 may be coupled to the motor/encoder 406 and may include a bend (for example, approximately 90 degrees). Thus, the motor/encoder 406 can detect rotational movement of the entire assembly including the manipulator ends 420, 422 and the motor/encoders 410, 412 and 414.

The motor/encoder 406 may be secured to a first portion 434 of the linear guide rail 409, which includes the first portion 434, the carriage 435 and the second portion 438, for example via the frame member 436. As described above, the motor/encoder 408 is coupled to the linear guide rail 409 to detect movement of the first portion (e.g., a sliding linear guide rail) 434 via a gear running on the second portion (e.g., a rack) 438 to detect movement of the first portion 434 relative to the carriage 435, which may be stationary, mounted to the frame member 441. Thus, the motor/encoder 408 can detect extension/retraction of the entire assembly including the manipulator ends 420, 422 and the motor/encoders 406, 410, 412 and 414.

The motor/encoder 404 may be coupled to the motor/encoder 408 via the bent frame member 441, which may be bent approximately 90 degrees. Thus, the motor/encoder 404 can detect rotational movement of the entire assembly including the manipulator ends 420, 422 and the motor/encoders 406, 408, 410, 412 and 414. The motor/encoder 402 may be coupled to the motor/encoder 404 via the joint element 403. The joint element 403 may be a frame member or a block that couples the motor/encoders 402 and 404 at different faces thereof. Bushings/washers (e.g., 405) may be provided between the motor/encoders 402 and 404 and the joint 403. The motor/encoder 402 may be secured to a frame member 442, which may be bent, for example at 90 degrees. The frame member 442 may provide the base 440. Thus, the motor/encoder 402 may detect rotational movement of the entire assembly with respect to the base 440.

When a position of the manipulator ends 420, 422 is changed by the surgeon, the motor/encoders 402, 404, 406, 408, 410, 412 and 414 can detect movement along the different axis of the manipulator 102 as described above. This movement can be directly correlated to movement along the respective axis of the in-vivo robotic manipulator. For example, extension of the linear guide rail 409 can directly correspond to extension of the robotic manipulator about axis 308; rotation of the motor/encoder 414 can directly correspond to rotation about the axis 314, etc. In particular, the degrees of movement may be constrained in a manner that corresponds to the freedom of movement of the robotic manipulator. Thus, the surgeon can easily control the precise positioning of the entire robotic actuator in addition to the relative location of the manipulator ends to the base. This allows for superior control of the robotic manipulator.

The described haptic feedback may be in the form of resistance, vibration, or other forms of feedback. The motor/encoders may also be capable of setting the manipulator 102 to a specified position. For example, at the beginning of an operation, the manipulator 102 may be driven to a starting position corresponding to the position of a corresponding robot manipulator. In this regard, the motor/encoders may have the capability of determining absolute position (for example, via a potentiometer) or relative position (for example, via a digital rotation segmented input).

The motor/encoders 402, 404, 406, 408, 410, 412 and 414 may directly correspond on a one to one basis with the axis of movement 302, 304, 306, 308, 310, 312 and 314 of the micro robotic actuator 350, shown in FIG. 4C. Thus, a surgeon's manipulator may be exactly mimicked for every axes of a corresponding in-vivo robot arm. This allows advantages such as a good feel of control and ergonomics for the surgeon.

Figure 4G:
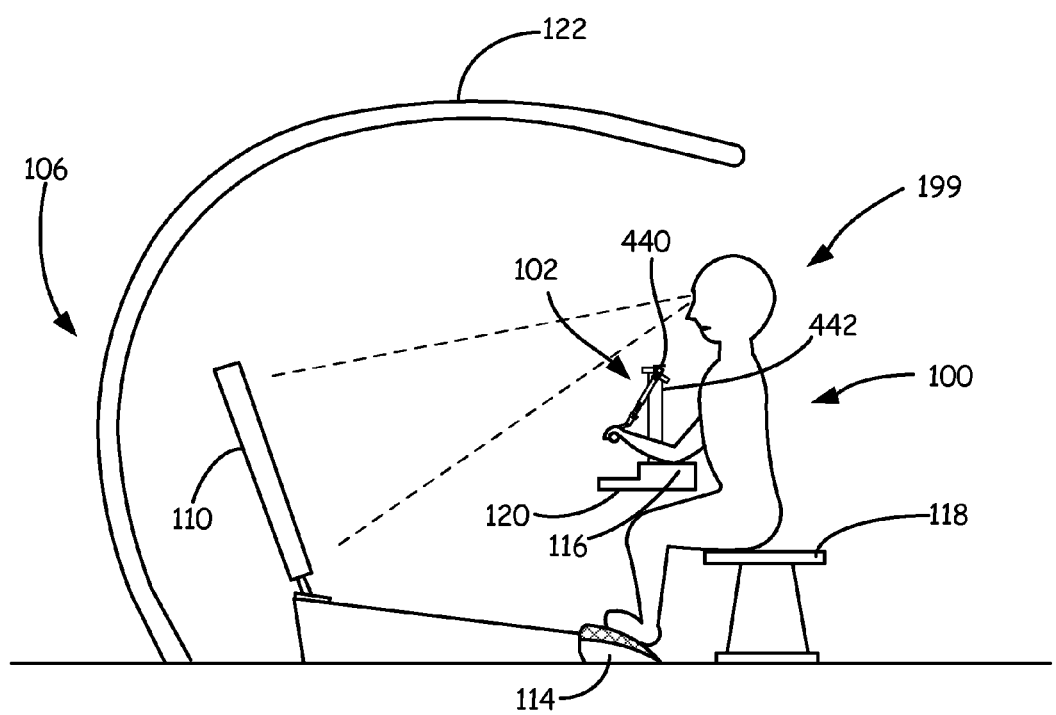
FIG. 4G is a side view of an exemplary surgeon console.

With reference to FIG. 4C, the base 340 of the robot manipulator 350 is generally attached to the inside of the abdominal wall, which in normal surgery will be on top. This arrangement of the manipulator end extending in a downward direction from a base of the robot manipulator may be emulated by positioning the anchor point 440 of the surgeon's manipulator 102 in the configuration as shown in FIG. 4G. The anchor point 440 of the surgeon's manipulator may be secured to a frame having a vertical member that positions the anchor member 442 above the arm rest 116. Thus, the surgeon's manipulator is provided in an orientation that corresponds with the orientation of the robot manipulator 340 during a surgical procedure. This orientation having a direct correspondence between the surgeon's manipulator and the robot manipulator makes direct, precision haptic feedback of each axis of movement to the surgeon possible.

Figure 5:
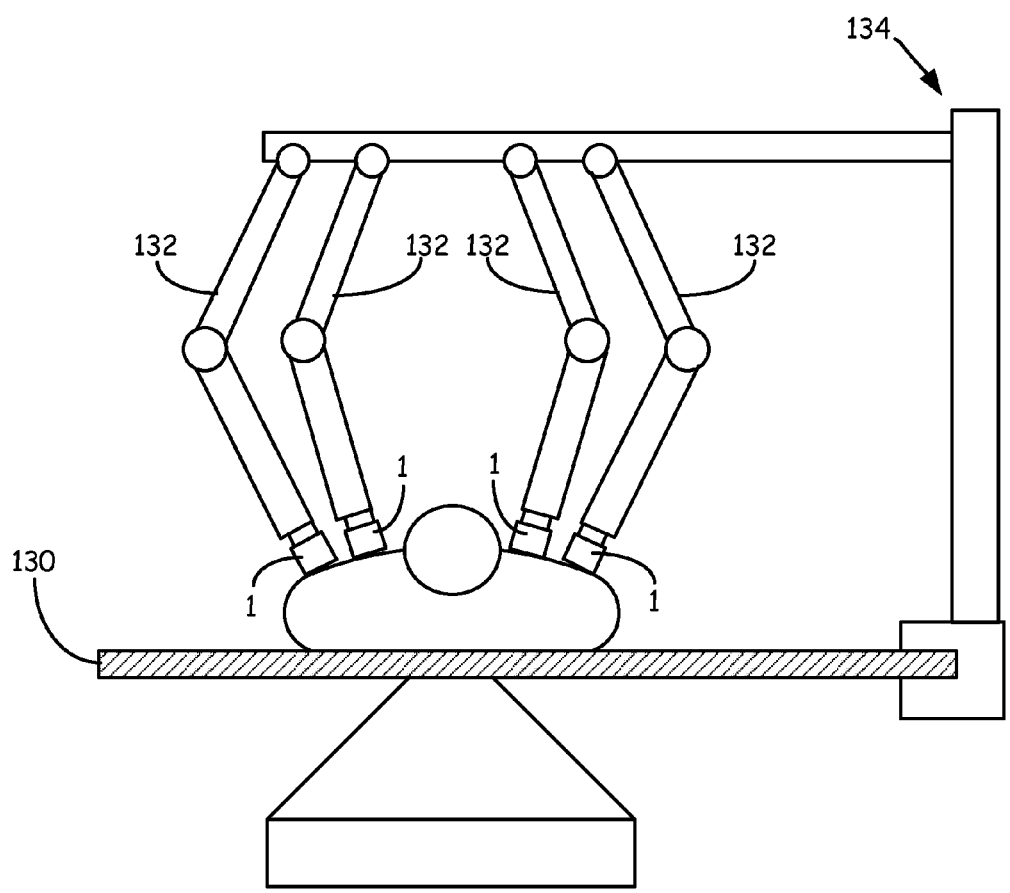
FIG. 5 is a side view of an exemplary patient table.

Referring to FIG. 5, an exemplary patient table 130 is shown. A plurality of the electromagnetic location fixing devices 1 may be coupled to arms 132. The arms 132, may be secured or coupled to the gantry 134, which is secured or coupled to the table 130. Thus, the whole system may move simultaneously with the patient. This allows for the changing of the position of the patient with the table intraoperatively without the need to undock the robotic system from the table and operations that require changes in patient position during the surgical procedure are facilitated. Also, the arms 132 may be servo driven for repositioning or adjusting an orientation of the electromagnetic location fixing devices 1.

Figures 6A, 6B:
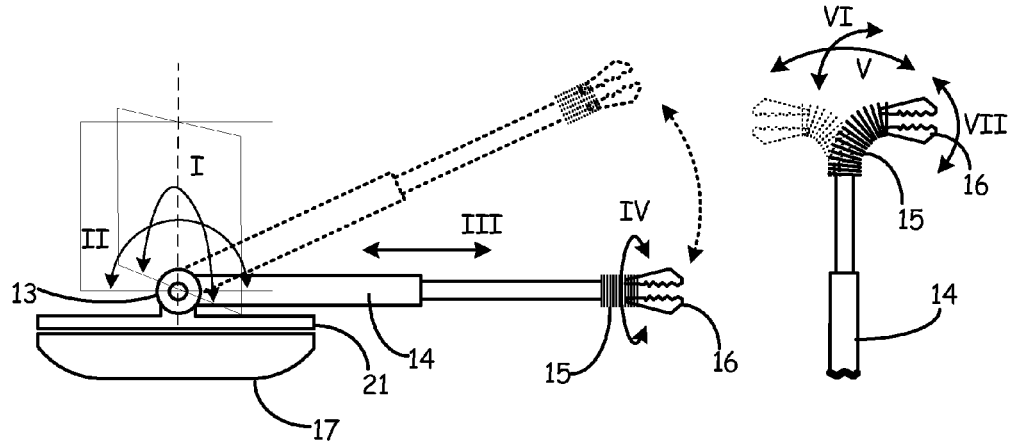
FIGS. 6A and 6B are side views showing 7-axis movement of an exemplary micro robotic manipulator.

Referring to FIGS. 6A and 6B, the axis of movement of the micro robotic manipulator 2 may have several different types of configurations. In the example shown in FIGS. 6A and 6B, 7-axis movement is shown. The joint 13 can rotate along the axes I and II, and the arm 14 can translate along direction III. The wrist 15 can rotate along axis IV, bend along axis V and bend along axis VI. A gripper/end effector 16 may also open and close along the axis VII, which could include rotational and/or translational movement. A portion of the micro robotic manipulator 2 having a joint with rotational axis similar to that of joint 13 and axes I and 2 as shown in FIG. 6 is referred to as Type A as a matter of convenience and is non-limiting.

Figures 7A, 7B:
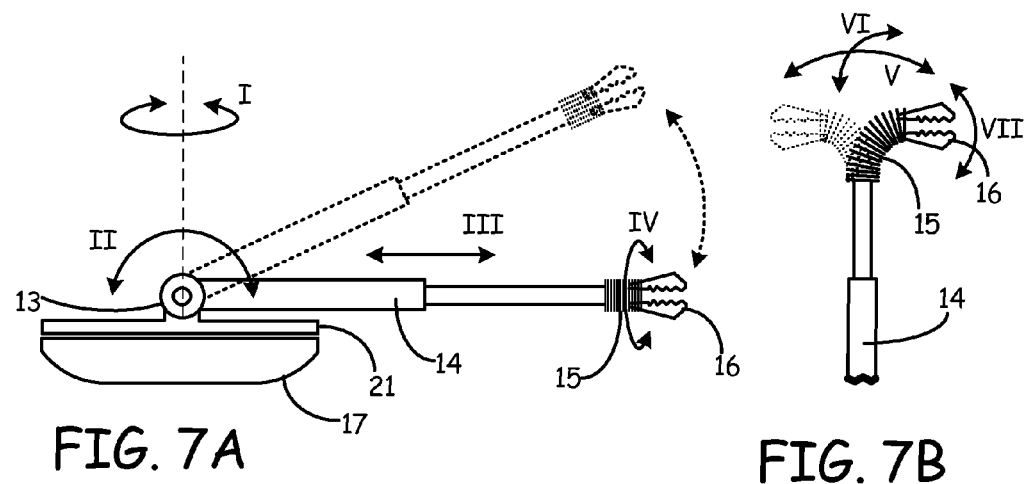
FIGS. 7A and 7B are side views showing 7-axis movement of an exemplary micro robotic manipulator.

FIGS. 7A and 7B show another configuration of the 7-axis movement of the manipulator 2 in which joint 13 rotates along axis I in another direction. A portion of the micro robotic manipulator 2 having a joint with rotational axis similar to that of joint 13 and axes I and II as shown in FIG. 7 is referred to as Type B as a matter of convenience and is non-limiting.

The enclosure of the manipulator 2 may facilitate the insertion of the manipulator into the body and protect the robotic arm and end effector inside the manipulator during insertion. It may include a base 21 and a pair of foldable flaps 17 on both sides of the base 21. As a non-limiting example, the flaps 17 may have a maximum diameter of 18 mm in a folded configuration. A maximum diameter of 18 mm is advantageous as it works well with an entrance port sized for use with most natural orifices.

Figures 8A, 8B:
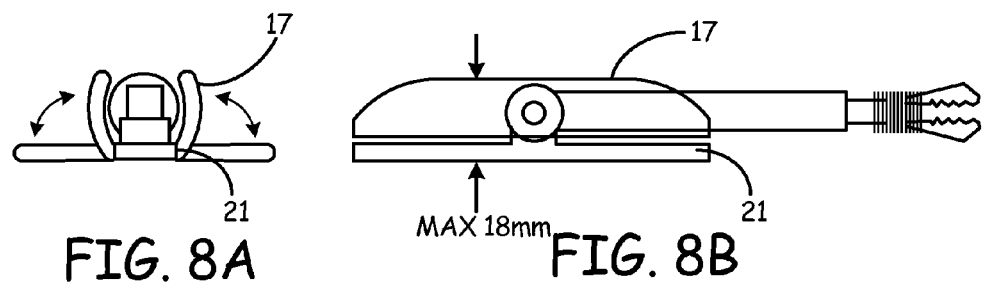
FIG. 8A is an end view and FIG. 8B is a side view of an exemplary foldable enclosure of a micro robotic manipulator.

During an initial state or insertion, the flaps are folded as shown in FIG. 8. Before deployment of the robot arm or end effector, the flaps 17 may be unfolded by a magnetic force triggered from the corresponding electromagnetic location fixing device 1.

The unfolding of the flaps 17 may be triggered by heat of the abdominal wall, by external radiation or by externally supplied power. For example, the base 21 may include a heating device activated by the supply of electrical current or by reception of a radiative energy from a transmitter included in the electromagnetic location fixing device 1. During removal from the body the flaps 17 may refold by cooling. The cooling may be effected by removing the electrical current or transmitted radiation supplied to the heating device and/or separating the manipulator 2 from the abdominal wall. The heating and cooling can also be achieved by other methods such as a thermo-electric heater/cooler, heat pipes, etc. This operation may be reversed with folding being triggered by heating and unfolding being triggered by cooling.

Alternatively or in addition, the flaps 17 may be a laminate of two materials having different coefficients of thermal expansion. Thus, as the flaps 17 are heated and cooled, the materials expand and contract at different rates causing the flaps 17 to fold and unfold. The materials may be metal alloys. The flaps 17 may be constructed from a shape memory alloy.

Alternatively or in addition, following the operation, the flaps 17 may be re-folded by manipulating the flaps 17 using another manipulator.

Alternatively or in addition, the flaps 17 may have a spring effect to assist in opening or closing the flaps and holding the flaps folded. For example, the flaps 17 may have a spring effect with a resultant force that tends to fold the flaps 17. In the presence of the fixing device 1, the spring effect is not strong enough to hold the flaps 17 folded and the flaps 17 are unfolded by the magnetic force. When the fixing device 1 is removed, the spring effect may cause the flaps 17 to fold.

Depending on the condition of the abdominal wall, translation motion of the flaps 17 may be provided by rollers on the flaps 17 (for example as shown by flaps 24 in FIG. 24) that are magnetically switchable or electrically actuatable.

Translation motion of the manipulator 2 may be provided by electromagnetic levitation. For example, the attractive force between the manipulator 2 and the electromagnetic location fixing device 1 may be lessened or reversed to permit movement with respect to the abdominal wall. The electromagnetic location fixing device 1 may then be moved on the abdominal wall by a servo or magnetic transport (similar to the electromagnetic fixing device 26 and base 25 shown in FIG. 24).

In the case of magnetic transport, magnets may be provided in the electromagnetic location fixing device 1. An externally supplied magnetic field is supplied to interact with the magnets of the electromagnetic location fixing device 1 or 26 to cause the electromagnetic location fixing device 1 to move in an X-Y direction and be repositioned with respect to the abdominal wall.

Figure 9:
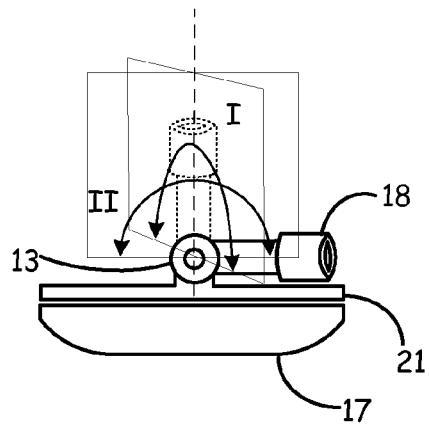
FIG. 9 is a side view showing 2-axis movement of an exemplary 2D micro robotic camera.
Figure 10:
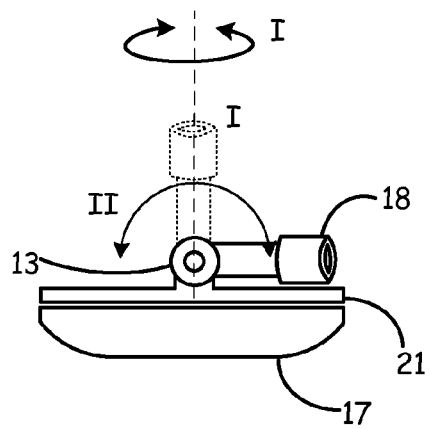
FIG. 10 is a side view showing 2-axis movement of an exemplary 2D micro robotic camera.
Figure 11A:
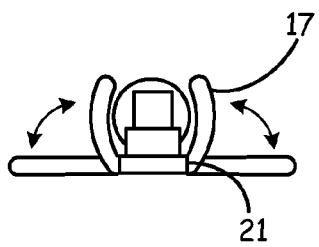
FIG. 11A is an end view and FIG. 11B is a side view of an exemplary foldable enclosure of a micro robotic 2D-camera.
Figure 11B:
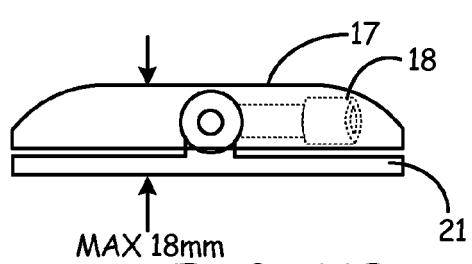
Figure 12:
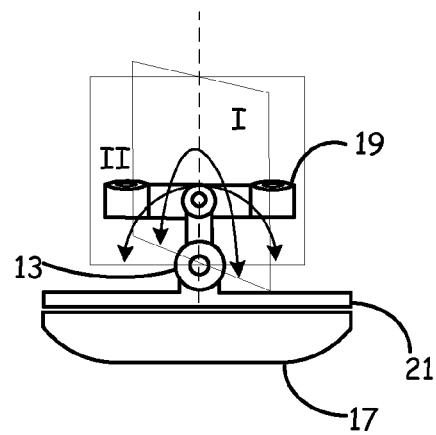
FIG. 12 is a side view showing 2-axis movement of an exemplary 3D micro robotic camera.
Figure 13:
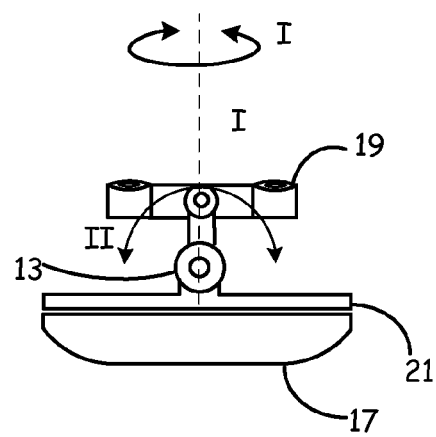
FIG. 13 is a side view showing 2-axis movement of an exemplary 3D micro robotic camera.
Figure 14A:
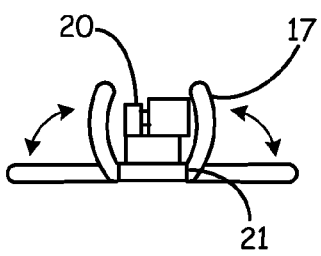
FIG. 14A is an end view and FIG. 14B is a side view of an exemplary foldable enclosure of a micro robotic 3D-camera.
Figure 14B:
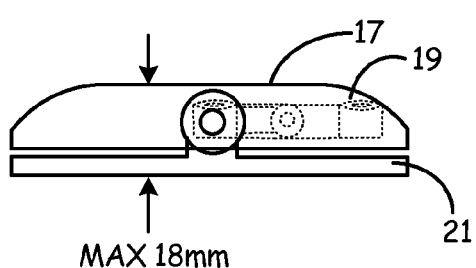

Depending on the purpose of the manipulator during operation, the end effector of the manipulator 2 may be adapted to a gripping device 16, an imaging device, such as a 2D video camera 18 or a 3D stereoscopic video camera 19, or other devices. In the case of a 2D or 3D camera, the camera may rotate along two perpendicular axes to acquire a 2D planar or 3D stereoscopic view in different orientations. Examples of two different types of configurations are shown in FIGS. 9 and 12 (Type A) and FIGS. 10 and 13 (Type B). The enclosure of the camera may facilitate the insertion of the manipulator into the body and protect the 2D camera or 3D camera inside the manipulator during insertion. During initial state or insertion of the 2D or 3D camera, the flaps are folded as shown in FIG. 11 and FIG. 14 respectively. As a non-limiting example, the flaps may have a maximum diameter of 18 mm. A maximum diameter of 18 mm is advantageous as it works well with an entrance port sized for use with most natural orifices. Before deployment of the 2D camera, the flaps 17 are unfolded by a magnetic force triggered from the corresponding remotely controlled electromagnetic location fixing device 1. A spring loaded rotational joint 20 may be included for a 3D camera, as shown in FIG. 14A.

Figure 15:
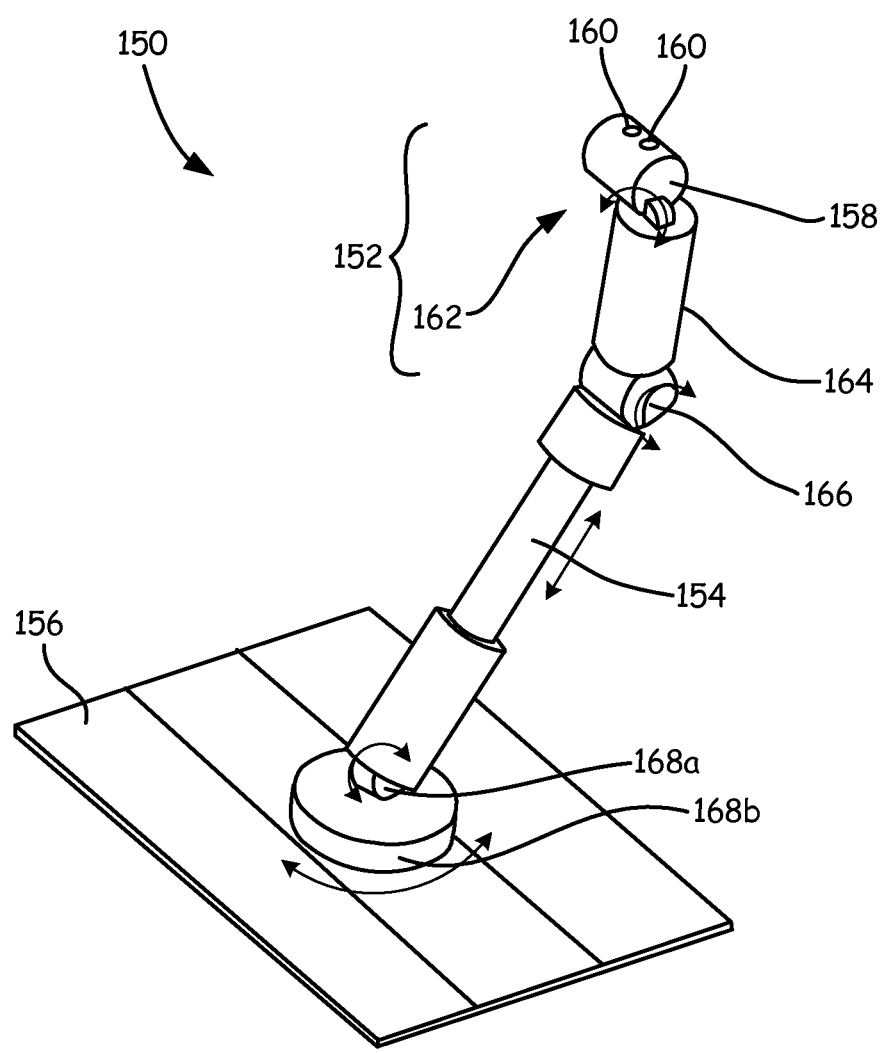
FIG. 15 is a perspective view of an exemplary 3D micro robotic camera.

FIG. 15 is a perspective view of an exemplary 3D camera 150. The camera 150 may include 3 parts: a camera body 152, an extendable linkage bar 154 and a foldable magnetic anchorage 156. The camera body 150 may include a swivel head 158 and two camera lenses 160. The camera lenses 160 may be spaced apart along a major axis of the swivel head 158 and provide a 3D image. The major axis of the swivel head may coincide with a longitudinal axis of the camera 150 in its folded configuration. Spacing the camera lens along the longitudinal axis or "side" accommodates both of the camera lenses 160, thereby providing 3D imagery not otherwise possible, in the limited diameter available in the implantable device. When a forward looking view is needed, the swivel head 158 can swing approximately 90 degrees (or more) to allow the "side" looking cameras to look forward.

A flexible linkage 162, which may be a hinge, is linked to a body part 164, which may be a tube or tube-like control unit. The body part 164 is linked to the extendable linkage bar 154 via a flexible linkage 166, which may be a hinge. The extendable linkage bar 154 extends and retracts to allow positioning of the camera body 152 near to the surgical field. An opposite end of the extendable linkage bar 154 is linked, and in some cases locked, to the foldable magnetic anchorage 156, for example, through a 2-axis flexible linkage 168a and 168b. The flexible linkages 162, 166, 168a and 168b may be servo driven. The foldable magnetic anchorage 156 may be secured on the abdominal/body wall, for example by activating an external magnet or positioning a permanent magnet outside the abdominal wall.

The flexible linkages 162 and 166 allow the camera 150 to bend and position in difficult and confined spaces while being secured by the anchorage 156. The foldable magnetic anchorage 156 may also be swiveled slightly with a center of rotation at the abdominal wall, for example by swiveling the external magnetic anchor, to facilitate slight sideway movement of the camera for clearer vision of an area of interest.

FIG. 16 show an exemplary micro robotic actuator 170 having 7 degrees of freedom and multiple axis of movement provided by the joints 172, 174, 178 and 180.

Additional anchoring force may be provided to the electromagnetic location fixing device 1. For example, for an obese patient with a thick abdominal wall (e.g., 50 mm thick or more), it may be difficult to sufficiently secure the electromagnetic location fixing device 1 to the manipulator 2 for precise motion during a surgical procedure. It is important that a stable platform be provided for secure anchorage of the miniature robots. Also, space available to accommodate the manipulators 2 having a small profile is limited. Thus, providing for external actuation may be desirable to provide sufficient torque for seven full axes of movement in the gripping and moving of organs or tissues during a surgical operation.

Figure 17:
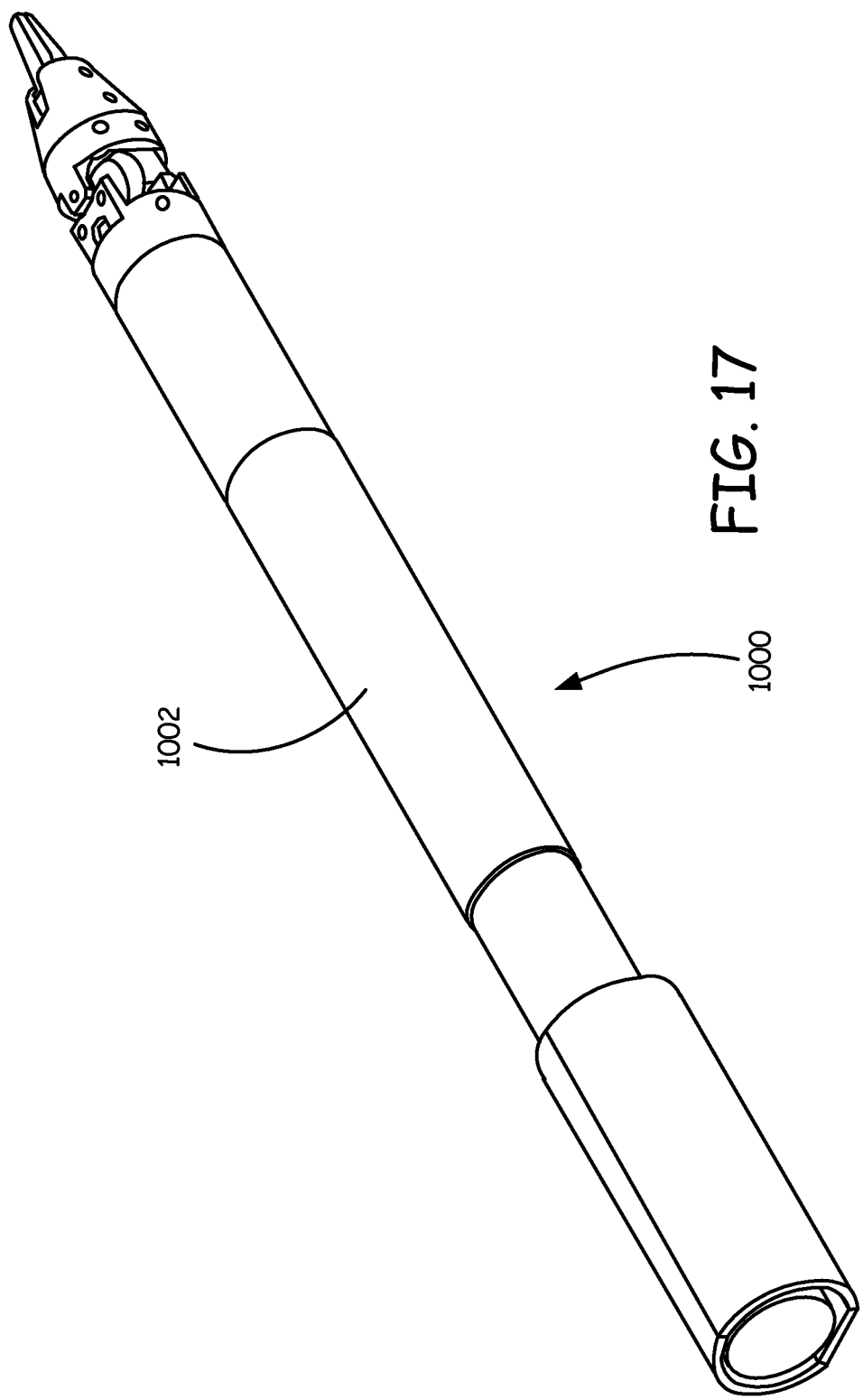
FIG. 17 is a perspective view of an exemplary micro robotic actuator in a folded state.
Figure 18:
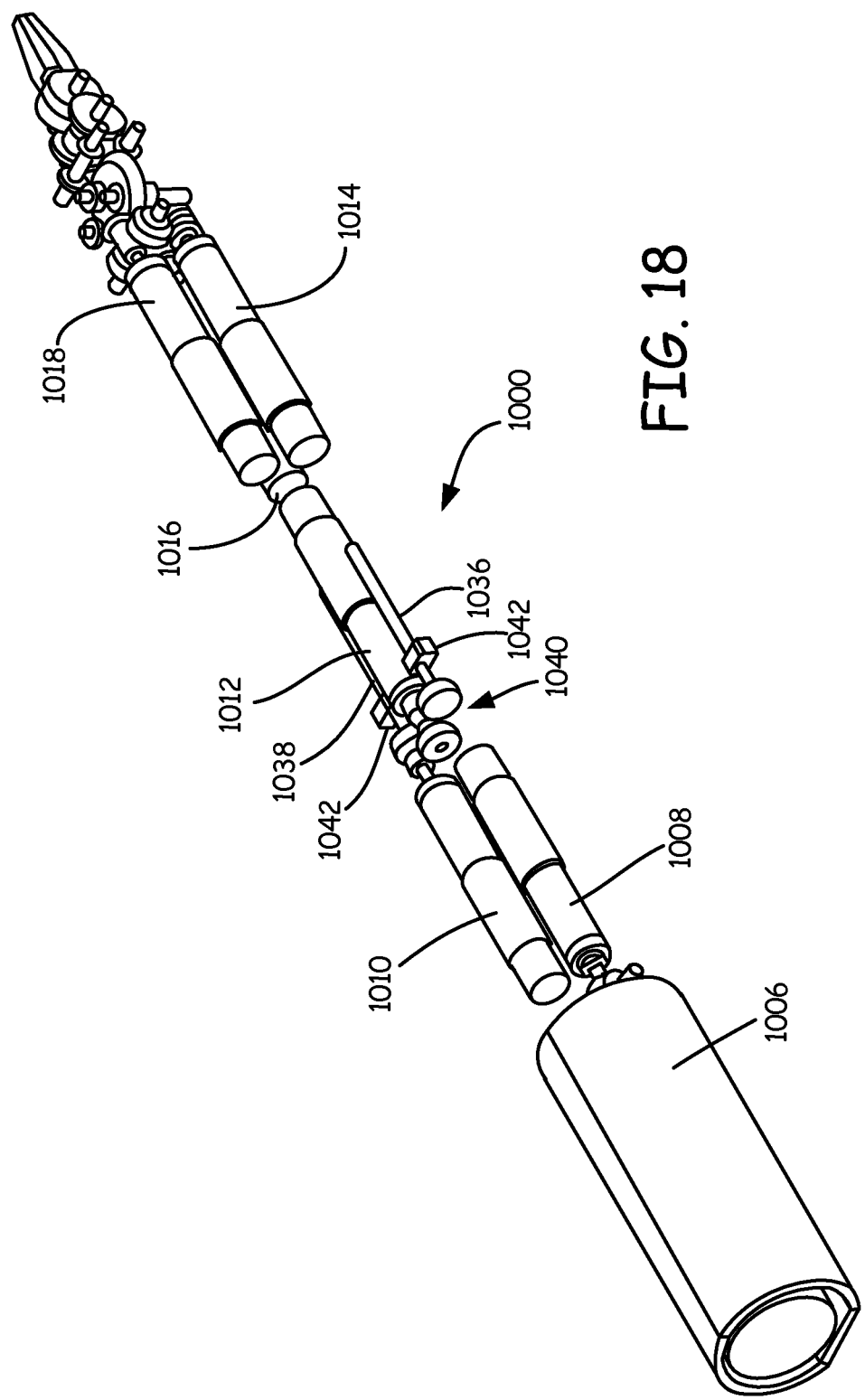
FIG. 18 is a perspective view of an exemplary micro robotic actuator in a folded state with the housing removed.
Figure 19:
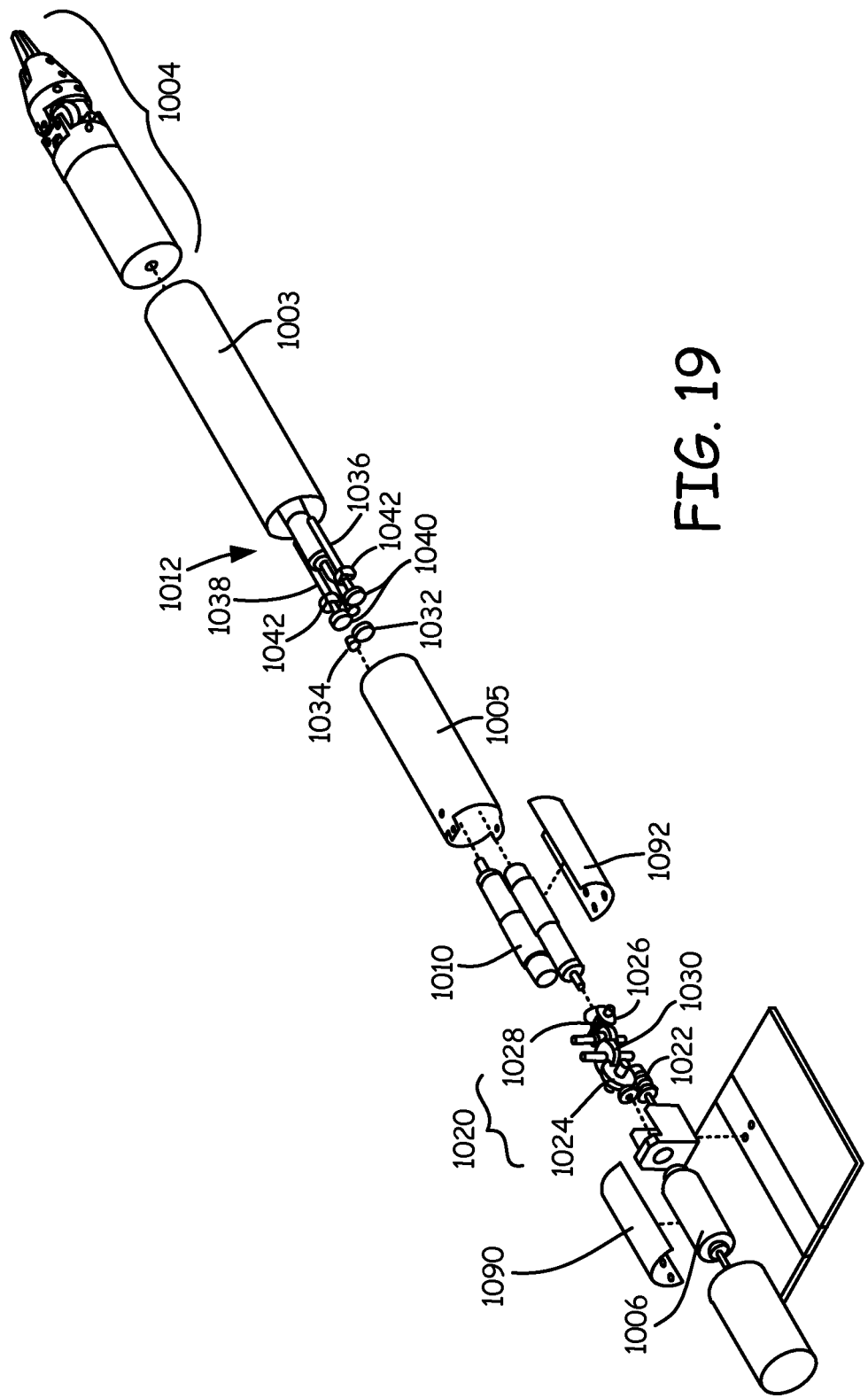
FIG. 19 is an exploded view of an exemplary micro robotic actuator.
Figure 20:
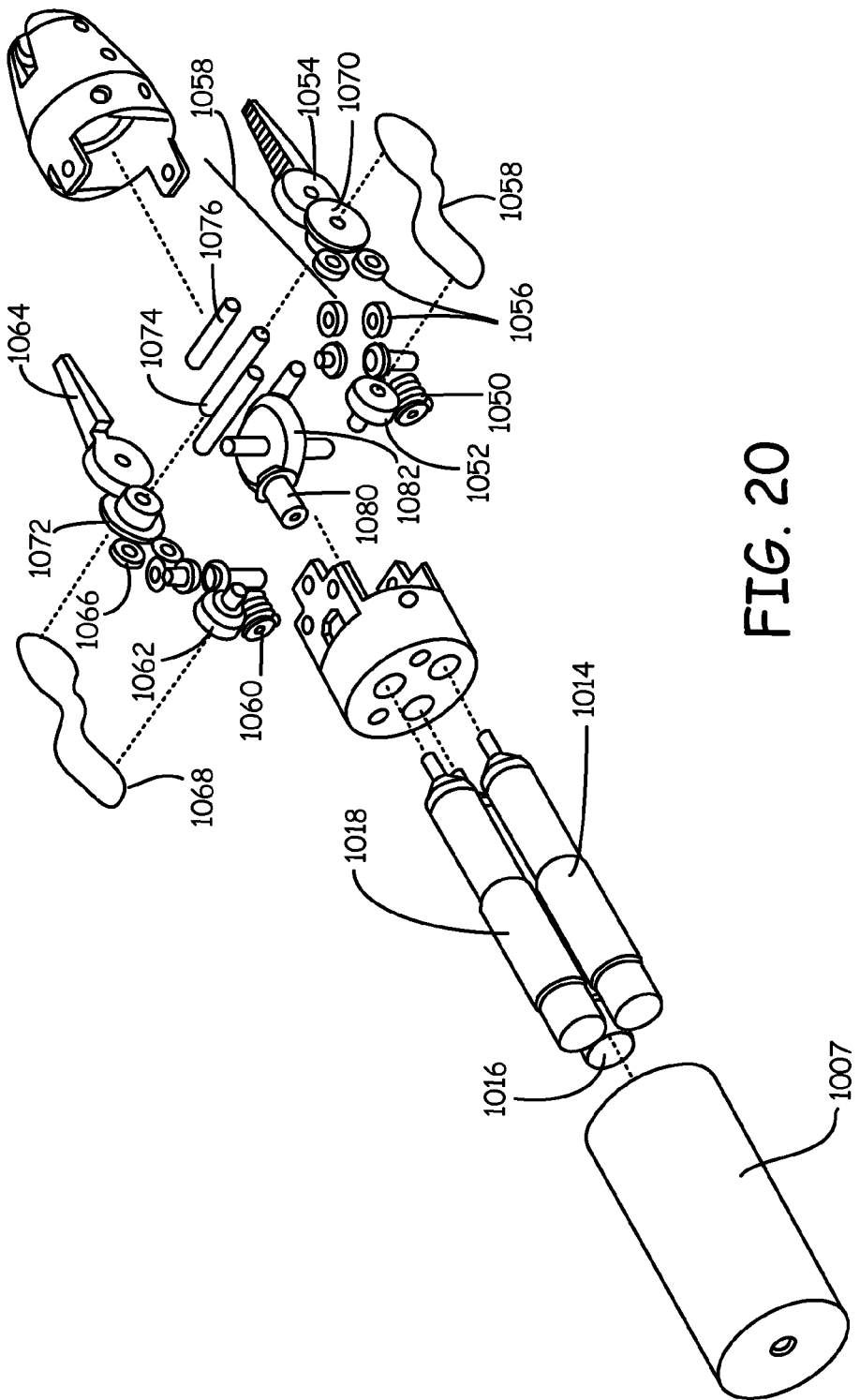
FIG. 20 is an exploded view of an exemplary end effector.
Figure 21:
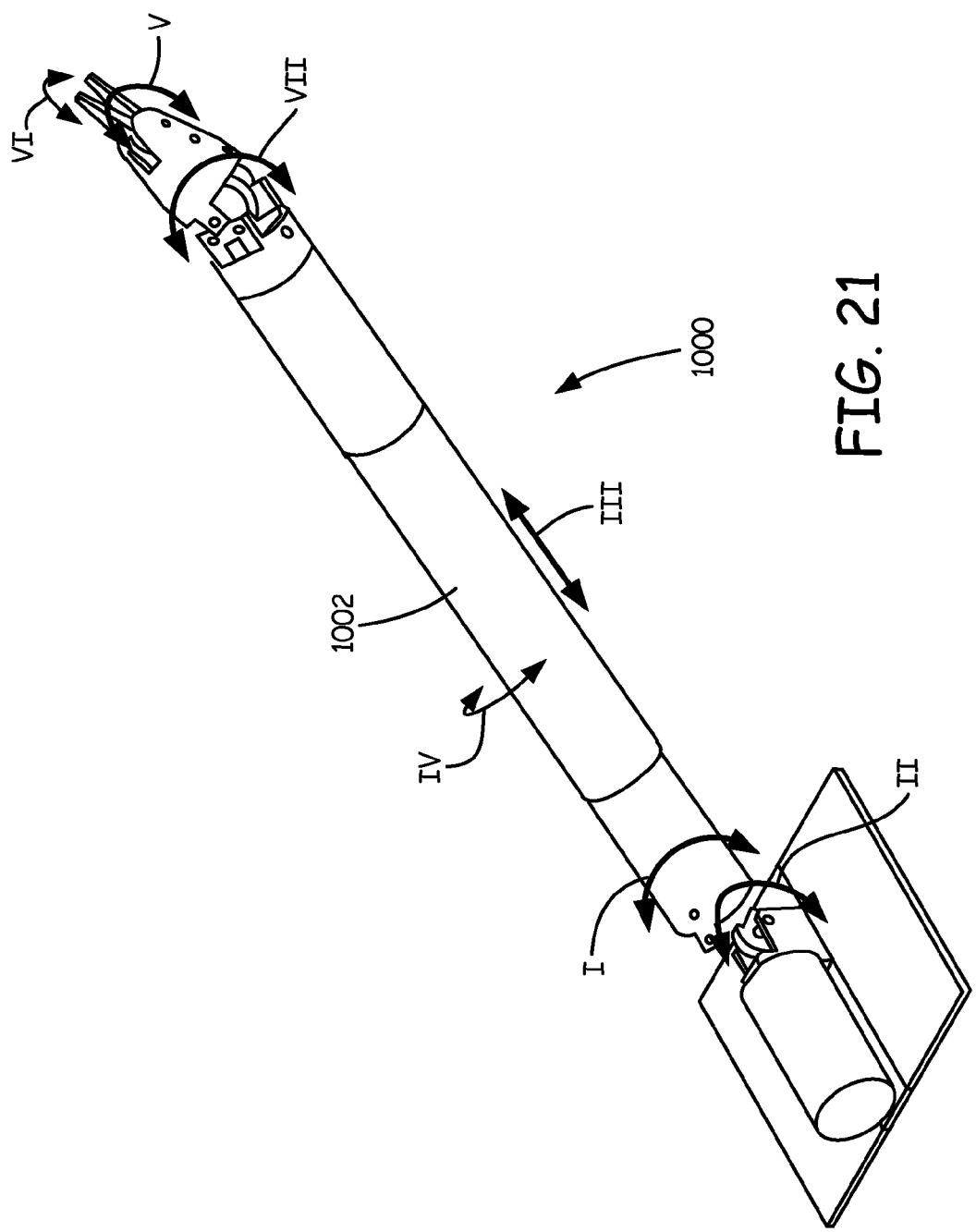
FIG. 21 is a perspective view of an exemplary micro robotic actuator in an unfolded state.
Figure 22:
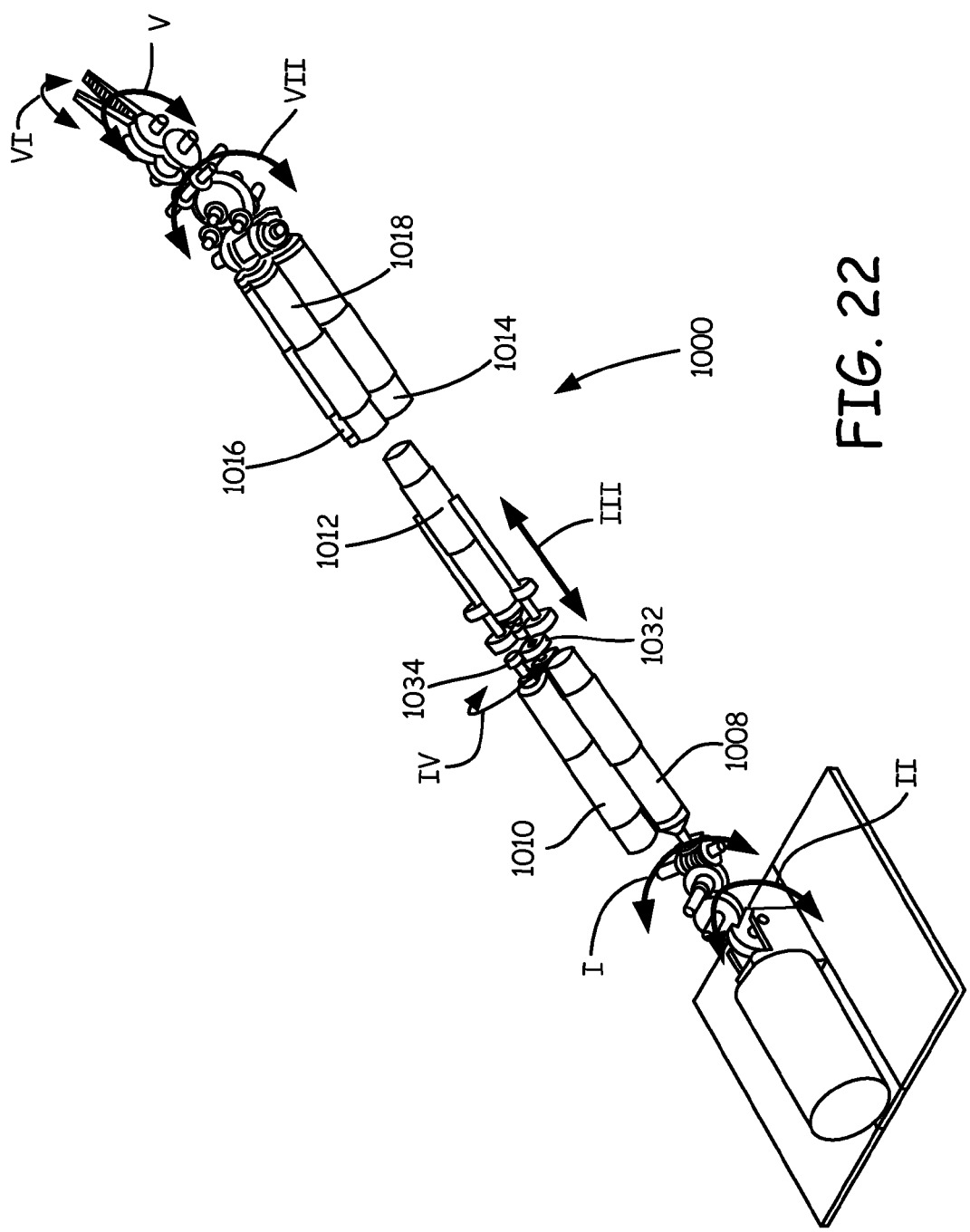
FIG. 22 is a perspective view of an exemplary micro robotic actuator in an unfolded state with the housing removed.

FIG. 17 shows an exemplary micro robotic actuator 1000 in a folded state including the housing 1002. FIG. 18 shows the exemplary micro robotic actuator 1000 in a folded state without the housing 1002. FIG. 19 shows an exploded view of the micro robotic actuator 1000. FIG. 20 shows an exploded view of the end effector 1004 of the micro robotic actuator 1000. FIG. 21 shows the micro robotic actuator 1000 in an unfolded state. FIG. 22 shows the micro robotic actuator 1000 in an unfolded state without the housing 1002. The following discussion refers to FIGS. 17-22 generically unless otherwise noted.

The micro robotic actuator 1000 includes the actuator/motors 1006, 1008, 1010, 1012, 1014, 1016 and 1018. The actuator/motors 1006, 1008, 1010, 1012, 1014, 1016 and 1018 provide in-vivo generation of force for the degrees of freedom (for example, seven) in an overall package size suitable for easy insertion into the human body through a single entrance port. For example, the micro robotic actuator 1000 in a folded configuration may be generally cylindrical with a diameter of 18 mm or less and a length of 200 mm or less.

Figure 16A:
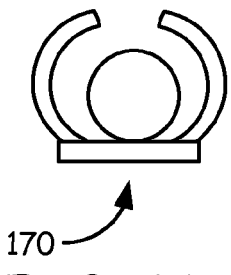
FIG. 16A is an end view of an exemplary micro robotic actuator in a folded configuration.
Figure 16B:
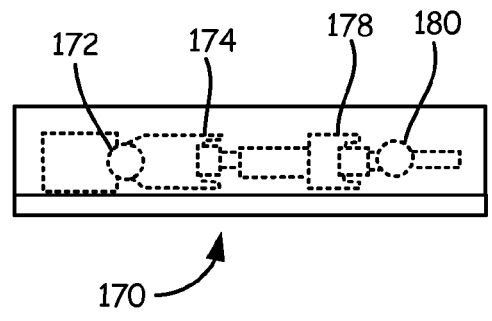
FIG. 16B is a side view of an exemplary micro robotic actuator in a folded configuration.
Figure 16C:
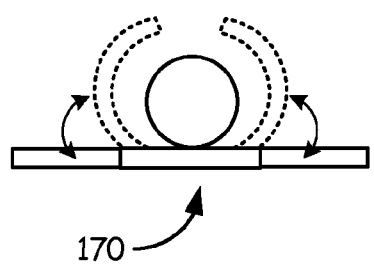
FIG. 16C is an end view of an exemplary micro robotic actuator in an unfolded configuration.
Figure 16D:
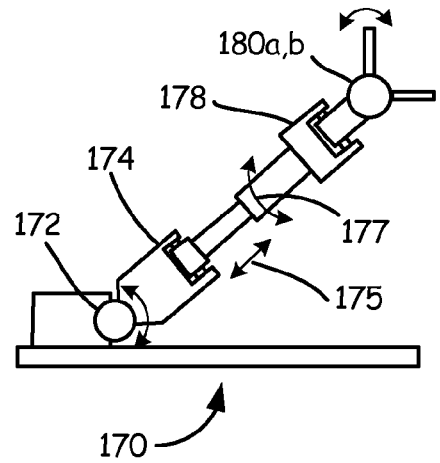
FIG. 16D is a side view of an exemplary micro robotic actuator in an unfolded configuration.

In the exemplary micro robotic actuator 1000 and also with reference to FIGS. 16B and 16D, the actuator/motor 1006 may provide rotation about the axis II at the joint 172; the actuator/motor 1008 may provide rotation about the axis I at the joint 174; actuator/motor 1010 may provide rotation about the axis IV at the joint 177; actuator/motor 1012 may provide extension and retraction along the axis III at the joint 175; actuator/motor 1014 may provide gripping action along the axis V at the joint 180a; the actuator/motor 1016 may provide gripping action along the axis VI at the joint 180b; and the actuator/motor 1018 may provide rotation about the axis VII at the joint 178.

For example, DC servomotors coupled with planetary gearboxes, spur gears and 90 degree intersecting worm gears may be installed at joints 172 and 174 near the manipulator base. Providing the servomotors near the joints allows for greater forces to be generated. For example, two motors may be located near the base of the micro robotic actuator to provide movement about two degrees of motion at the base, one motor may be proved at a central portion of the micro robotic actuator to provide extension/retraction and three motors may be located distal to the two base motors and proximal to the end effector to provide movement about three degrees of motion at the manipulator end of the micro robotic actuator.

In some examples, 1-2 Nm torque for loading force along axis I and II may be generated. Gripping forces for forceps and needle drivers approximately ~10 N and ~20 N respectively may be generated by a combination of piezoelectric actuators and miniature DC servomotors installed in the vicinity of joints 178 and 180. This torque and force is sufficient to perform various manipulations required by surgical operations. The extension and rotation of the manipulator may be controlled by the piezoelectric actuators and DC servomotors installed at joints 175 and 177 respectively.

The actuator/motor 1006 may be coupled to the actuator/motor 1008 via the gear assembly 1020. The gear assembly 1020 may include a worm gear 1022 coupled to the actuator/motor 1006 and the gear 1024. Rotation of the actuator/motor 1006 output may then provide rotation about the gear 1024 to provide the rotation about the axis II at the joint 172. The gear assembly 1020 may also include a worm gear 1028 coupled to the actuator/motor 1006 and the gear 1028. Rotation of the actuator/motor 1008 output may then provide rotation about the gear 1026 to provide the rotation about the axis I at the joint 174. The gear 1024 and the gear 1028 may be coupled via the gear 1030 that may be secured to the housing 1002. The use of a 90 degree intersecting gears 1024 and 1030 is a simple, compact and light weight way to provide X-Y swing movement along the axes I and II directions. The integrated worm and wheel mechanism may provide increased torque (e.g., 1-2 Nm) about the axes I and II.

The actuator/motors 1008 and 1010 may be fixed together directly or via the housing 1002. The output of the actuator/motor 1010 may be coupled to the gear 1032, which may be secured to the housing 1002, to provide the rotation about the axis IV at the joint 177.

The actuator/motor 1012 may be coupled to the threaded rods 1036 and 1038 via the gear system 1040. The carriers 1042 may be fixed to the portion 1003 of the housing 1002. As the output of the actuator/motor 1012 rotates, the carriers 1042, which are fixed to the portion 1003, travel along the threaded rods 1036 and 1038 thereby causing the portions 1003 and 1005 of the housing 1002 to extend or retract with respect to each other.

In some examples, the actuator/motor 1012 may be in the form of a DC servo motor or several piezo-electric motors along the circumference of the robot arm. In such an example, the threaded rods 1036 and 1038 may not be included.

The actuator/motor 1014 may be coupled to the worm gear 1050. The worm gear 1050 may be coupled to the gear 1052, which is coupled to the manipulator end 1054 via a pulley system 1056 that includes the wire or belt 1058. The actuator/motor 1016 may be coupled to the worm gear 1060. The worm gear 1060 may be coupled to the gear 1062, which is coupled to the manipulator end 1064 via a pulley system 1066 that includes the wire or belt 1068. The pulley systems 1056 and 1066 end at the pulleys 1070 and 1072 respectively that share the common shaft 1074. The pulleys 1070 and 1072 are free to rotate about the common shaft 1074 individually. The pulleys 1070 and 1072 may be coupled to the manipulator ends 1054 and 1064 via gear teeth allowing for rotation of the manipulator ends 1054 and 1064 about the common shaft 1076 to provide the gripping action along the axes V and VI at the joints 180a and 180b.

The gears 1052 and 1062 may be planetary gearboxes to provide a speed reduction and force multiplication of the output of the actuator/motors 1014 and 1016. The flexibility in the pulley systems 1056 and 1066 coupled to the planetary gear boxes provide mechanical advantage as well as freedom of movement. The final connection to the manipulator ends 1054 and 1064 may be geared to increase gripping force at the tip of the manipulator. The gear ratios of the planetary gear boxes and the gearing at the manipulator ends may be different. Also, the use of dual worm gears (1050 and 1060) and dual actuator/motors (1014 and 1016) allows for increased torque at minimum distance. Thus, increased gripping forces such as 10-20 N can be realized.

The actuator/motor 1018 may be coupled to the gear 1080, which is coupled to the gear 1082. The gear 1082 may be secured to the portion 1007 of the housing 1002 to provide rotation about the axis VII at the joint 178. The gear 1080 may be beveled and intersect with the gear 1082 at an approximately ninety degree angle.

The micro robotic actuator 1000 may include the circuit boards 1090 and 1092. The circuit boards 1090 and 1092 may be flexible (e.g., flexible PCB circuitry) to conform to the shape of the housing 1002, such as a cylinder and may be disposed along an inner wall of the housing 1002. The circuit boards 1090 and 1092 may include driver electronics and/or integrated networking capability. Including the driver electronics and/or integrated networking capability within the micro robotic actuator 1000 allows for the reduction of external cabling to fewer conductors in a wire bundle or fewer wire bundles overall.

Figure 25:
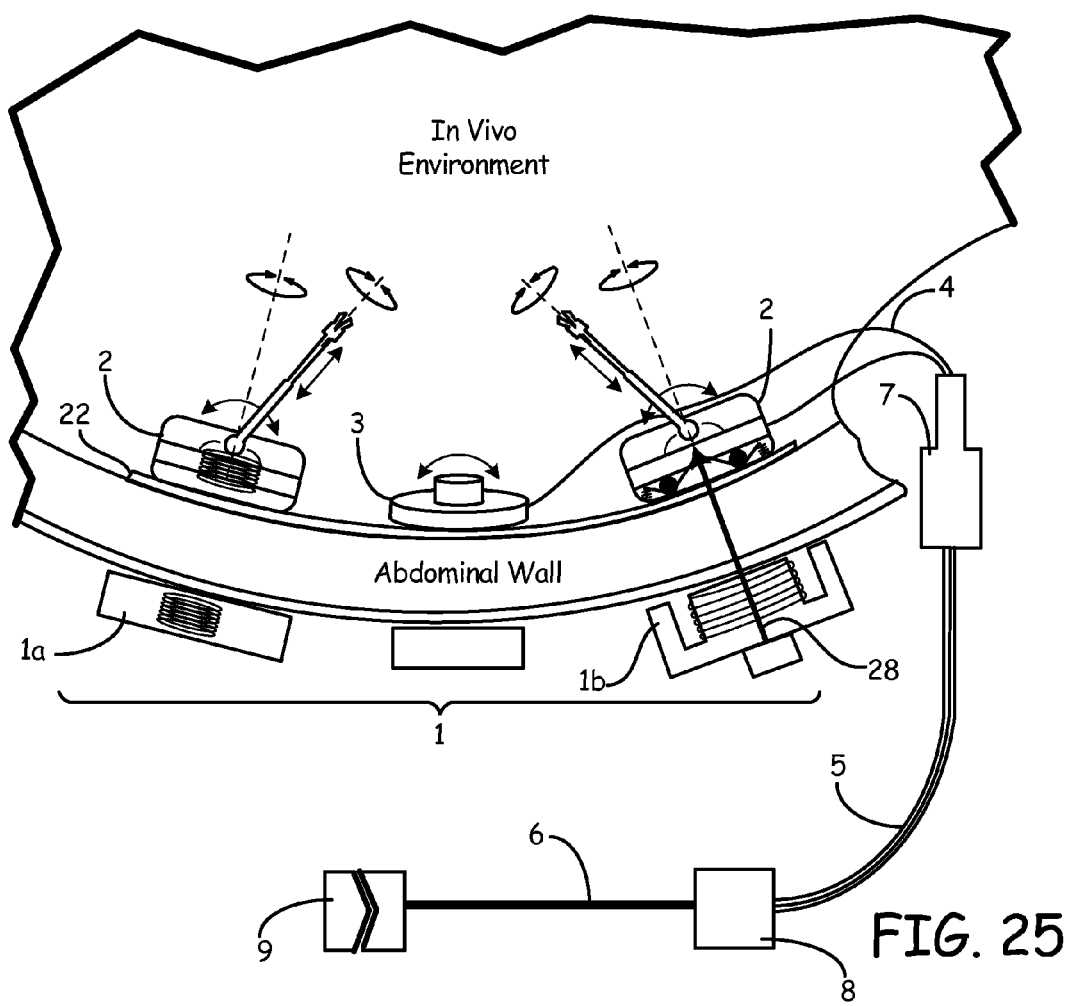
FIG. 25 is a schematic view of an exemplary surgical robotic system including a fine metal wire.
Figure 26A:
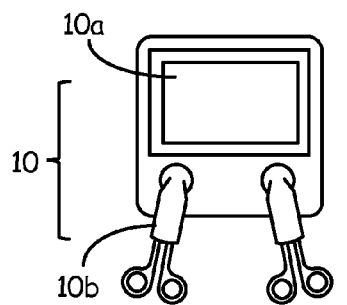
FIGS. 26A and 26B are front views of exemplary human machine interfaces.
Figure 26B:
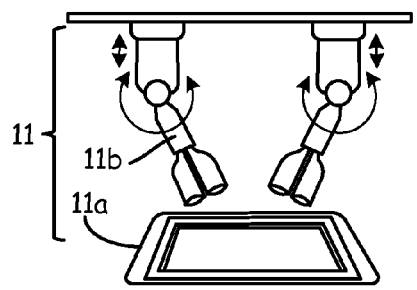
Figure 27:
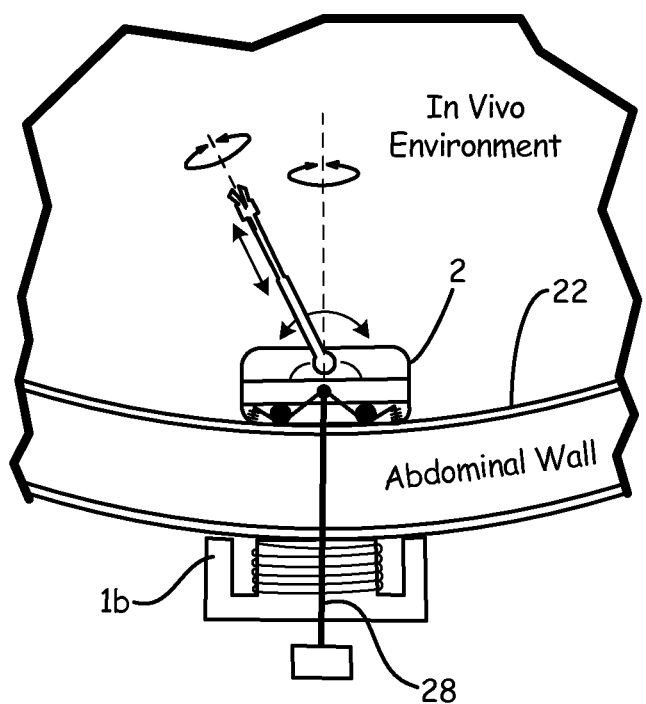
FIG. 27 is a side view showing insertion of an exemplary fine metal wire.

Referring to FIGS. 25-27, a flexible or semi-flexible magnetic sheet 22 can be inserted into the body cavity through the entrance port 7. When inserted, the magnetic sheet 22 may be rolled or folded. Once inserted, it can be unfolded or unrolled and positioned along the abdominal wall. The magnetic sheet 22 may be unfolded/unrolled by a mechanical mechanism or it may be unfolded/unrolled by subjecting it to a magnetic field, which may be supplied by an external electromagnet, and/or by heating or cooling through supplied energy.

The magnetic sheet 22 may be provided as a single large sheet sufficient to cover a large area of the inner abdominal wall. The magnetic sheet may also be provided by one or more small or medium sized sheets to provide coverage for a certain region of the abdominal wall.

Figure 34:
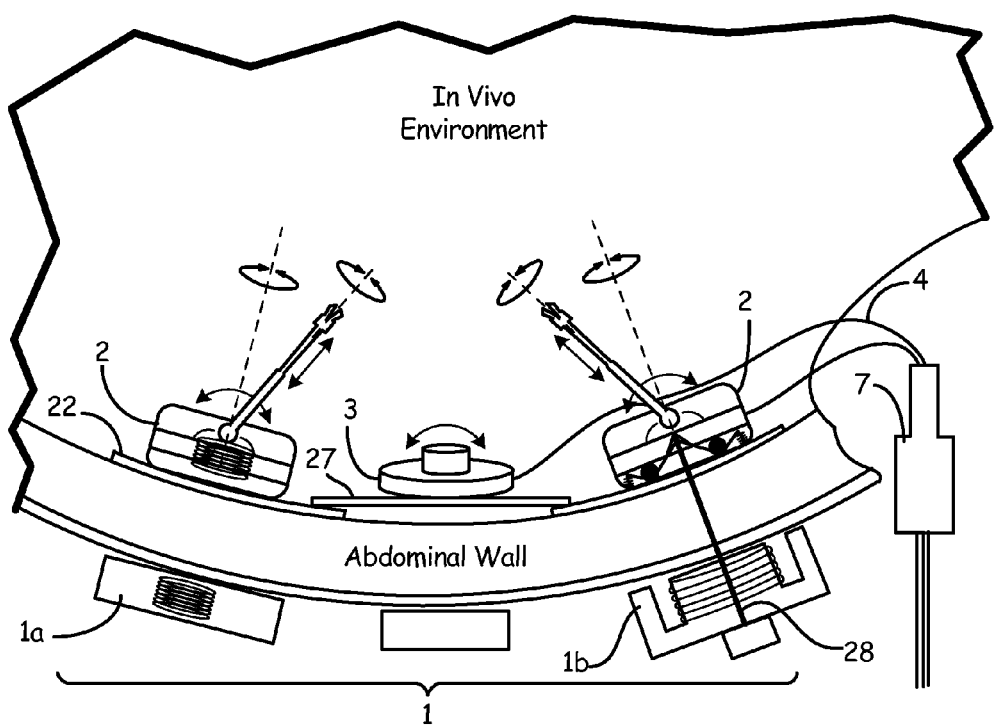
FIG. 34 is side view of an exemplary intra abdominal mechanical frame.

An intra abdominal mechanical frame, for example the intra abdominal mechanical frame 27 shown in FIG. 34, may be constructed by linking individual magnetic sheets with extendable bars to provide a stable platform for the miniature robots to operate. This intra abdominal mechanical frame may, in some cases, provide anchoring support similar to that of a large flexible magnetic sheet covering a large part of the abdomen without requiring the use of such a large sheet.

The position of the magnetic sheet 22 may be fixed by the external electromagnet 1b. The magnetic sheet 22 provides a stable platform for the micro robotic manipulator 2 to attach to. The magnetic sheet 22 may provide a medium to concentrate magnetic flux and provide for the secure anchorage of micro robotic manipulators such as the micro robotic manipulator 2. Exemplary materials that provide such a medium to concentrate flux include iron and silicon-iron based materials. It will be appreciated that this secure anchorage can be provided for any micro robotic manipulator as well as other related devices such as a camera. It will also be appreciated that the magnetic sheet may be used with, but is not required for, any of the described examples including those of FIGS. 1 and 23-34.

To provide additional anchorage force, a fine wire 28 may be included. The fine wire 28, which may be a metal wire, extends from the external electromagnet 1b and may be introduced through the abdominal wall via, or in the form of, a fine needle. To facilitate introduction of the fine metal wire 28 via a needle or hypodermic syringe, the wire 28 may have a maximum diameter of 1 mm. A maximum diameter of 1 mm is preferable so that punctures remain well below a size that would be regarded an incision and leave no significant visible scarring. It will be appreciated that other materials such as flexible or rigid fibers, biocompatible polymers/plastics and multi-material composites that may or may not include a metal may be used in place of metal for the wire 28.

As an example, the fine metal wire 28 may be provided from the external electromagnet 1b via a circular through hole, a slot, or another aperture in the electromagnet 1b. The hole, slot or other aperture may be provided at a center of the electromagnet 1b.

A locking mechanism, such as a pair of inclined metal tabs having a separation less than a thickness of the fine wire 28 or a tip thereof, may be provided to releasably lock the micro manipulator 2 on the tip of the fine wire 28. In the example of a locking mechanism using a metal tab, the metal tab may be subject to a biasing force, such as a spring, to keep the fine wire 28 locked in the micro robotic manipulator 2. Removing the biasing force or providing a counter force may allow the fine wire 28 to be released. The release of the fine wire 28 may be provided by a remote controlled electrical actuator or by mechanical action, for example by an endoscope, inside the abdomen.

Figure 28:
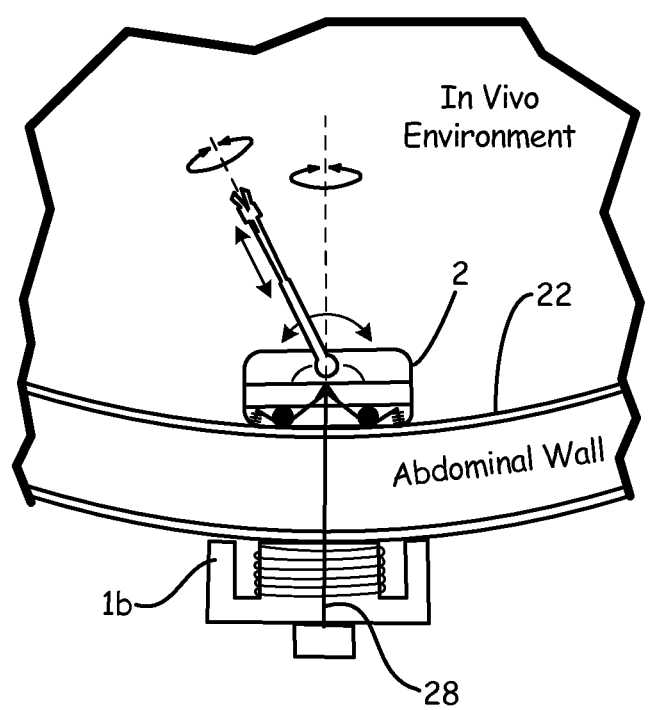
FIG. 28 is a side view showing locking of an exemplary fine metal wire to a miniature robot.

Referring to FIG. 28, the tip of the metal wire 28 may be locked by a releasable non-return mechanism. The tip of the fine wire 28 may be enlarged to provide a more secure lock.

Figure 29:
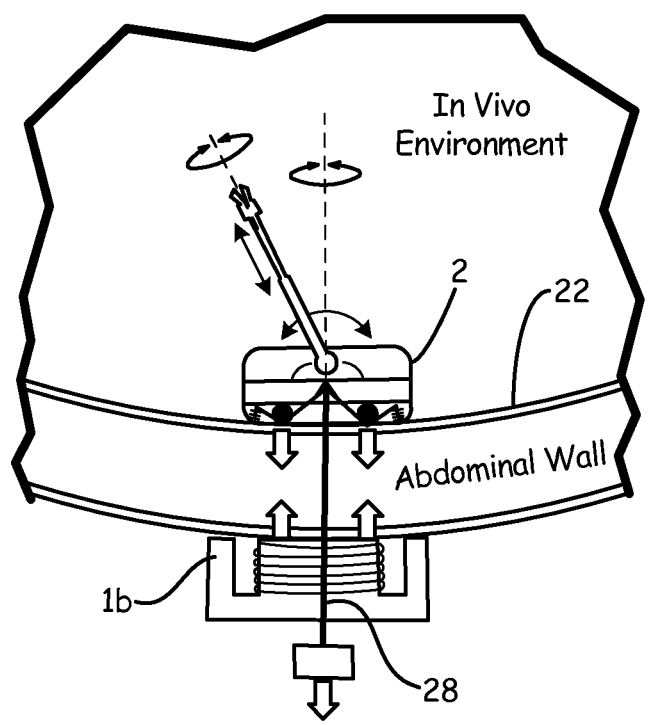
FIG. 29 is a side view showing an example of force of tightening by a fine metal wire.
Figure 30:
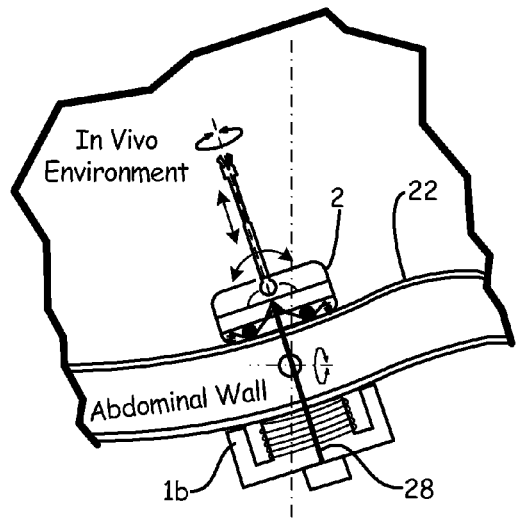
FIG. 30 is a side view showing exemplary X-Y movement of a micro robotic manipulator to the left with a fine metal wire.
Figure 31:
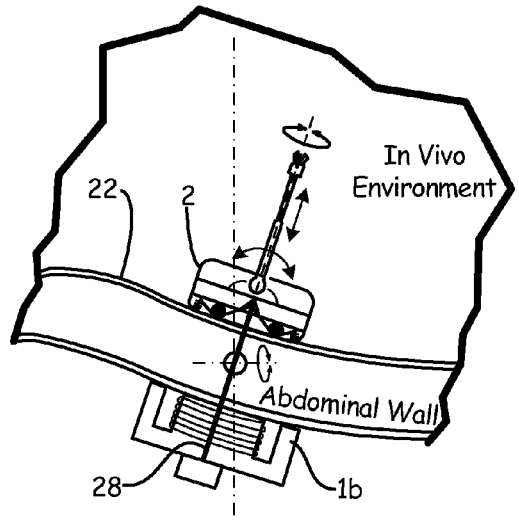
FIG. 31 is a side view showing exemplary X-Y movement of a micro robotic manipulator to the right with a fine metal wire.
Figure 32:
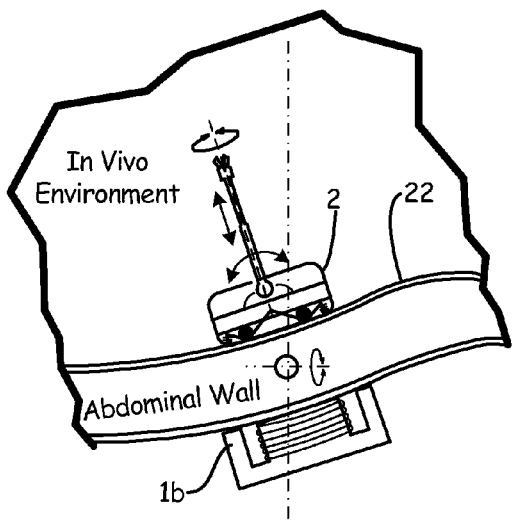
FIG. 32 is a side view showing exemplary X-Y movement of a micro robotic manipulator to the left without a fine metal wire.
Figure 33:
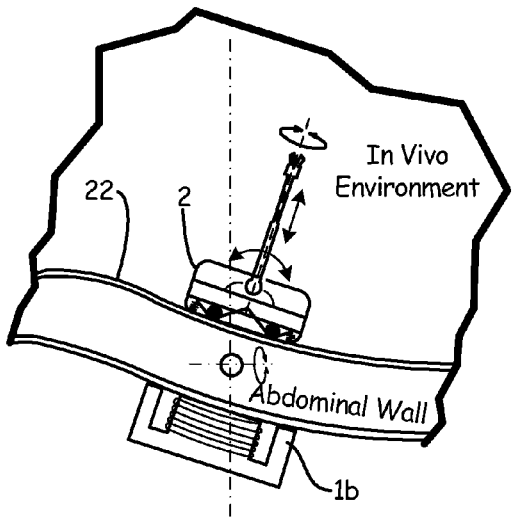
FIG. 33 is a side view showing exemplary X-Y movement of a micro robotic manipulator to the right without a fine metal wire.

Referring to FIG. 29, when the fine wire 28 is tightened at the base of the external electromagnet 1b, the external electromagnet 1b and the miniature robot 2 are pressed against the abdominal wall from opposite sides such that an additional locking force is provided for the micro robotic manipulator 2 to attach to the stable platform. Therefore, secure and stable movements of the micro robotic manipulator 2 are provided in carrying out the surgical operation.

An aperture may be provided in the external electromagnet 1b through which the fine wire 28 passes. The aperture may be in the form of a slot, a cross, a large singular opening, or another shape. Providing the aperture allows for the relocation of the micro robotic manipulator 2 after the fine wire 28 has been inserted in the abdominal wall without requiring a reinsertion of the fine wire 28. Thus, the wire may be loosened allowing the movement of the external electromagnet 1b and the micro robotic manipulator 2 and subsequently retightened to allow for the repositioning of the micro robotic manipulator 2.

In addition to providing additional anchorage force, the fine wire 28 may also be used to supply power or signals to/from the micro robotic manipulator 2.

Referring to FIGS. 30-33, when the miniature robot is tightly coupled to the electromagnet, movement of the micro robotic manipulator 2 may be induced by the swivel action of external electromagnet 1b. For example, the center of movement may be located at the midpoint of the abdominal wall.

The external actuation can supplement the X-Y movement of micro-actuator on the micro robotic manipulator 2. Due to the leverage effect, a small angular movement of the electromagnet 1b will lead to a large two dimensional X-Y movement of the micro robotic manipulator 2. Without the tight coupling, attempts to move the micro robotic manipulator 2 in this manner would likely result in separation of the micro robotic manipulator 2 and the external electromagnet 1b and X-Y movement would not be achieved.

Although the above described provision of additional anchorage force has been described in the context of a micro robotic manipulator and an external magnet, it will be appreciated that this is merely an exemplary application and the described apparatus and methods can also be applied to any of a variety of other instruments in which anchorage onto a stable platform inside a body cavity is desired.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages. In particular, and unless otherwise stated, the various features and aspects of the described embodiments may be used separately and/or interchangeably in any combination and are not limited to the arrangements described above.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

The invention claimed is:

1. A robotic actuator, comprising:
an internal anchor that is adapted to be inserted into a body via an entrance port, positioned inside the body, and magnetically coupled with an external anchor positioned outside the body; and
an instrument assembly that is adapted to be inserted into the body via the entrance port, wherein the instrument assembly is secured to the internal anchor, the instrument assembly comprising:
an arm having a serial arrangement of a proximal segment, a middle segment, and a distal segment, wherein:
a proximal end of the proximal segment is pivotally secured by a joint to the internal anchor in such a way that the proximal segment is configurable to pivotally move relative to the joint according to the joint's pivotal connection of the proximal end and the internal anchor;
each of the proximal segment, middle segment, and distal segment having an elongated hollow body; and
the middle segment is provided between the proximal and distal segments, the middle segment configurable to rotate relative the proximal segment, the rotation of the middle segment being a rotation relative to an axis formed by the middle segment;
an end-effector, the end-effector having a wrist and an instrument, the instrument secured by the wrist to a distal end of the distal segment via the wrist in such a way that the instrument is configurable to pivotally move relative to the wrist according to the wrist's pivotal connection of the distal end and the instrument;
a plurality of actuators distributed on the arm, wherein the elongated hollow body of the proximal segment houses at least one of the actuators, wherein each of the plurality of actuators comprises a multi-axis robotic joint, and wherein each of the plurality of actuators provides multiple degrees of movement via multiple axes relative to the internal anchor; and
one or more sensors provided on the instrument assembly, the one or more sensors configured to detect a resisting force resulting from the pivotal movement of the proximal segment relative to the joint, the rotational movement of the middle segment, or the pivotal movement of the instrument relative to the wrist, the one or more sensors providing a corresponding haptic feedback to a manipulator when a resisting force is detected;
wherein the pivotal movement of the proximal segment relative to the joint, the rotational movement of the middle segment, and the pivotal movement of the instrument relative to the wrist are each controllable by the manipulator.

2. The robotic actuator of claim 1, wherein the actuators each have a rotation axis oriented in a same direction.

3. The robotic actuator of claim 2, wherein the actuators are distributed along the rotation axis.

4. The robotic actuator of claim 3, wherein the plurality of actuators includes a first actuator proximal to the internal anchor, a second actuator proximal to the wrist, and a third actuator disposed between the first and second actuators.

5. The robotic actuator of claim 4, wherein
the first actuator is configurable to provide the pivotal movement of the proximal segment relative to the joint,
the second actuator is configurable to provide the pivotal movement of the instrument relative to the wrist, and
the third actuator is configurable to provide the rotational movement of the middle segment.

6. The robotic actuator of claim 5, further comprising a fourth actuator, the fourth actuator configurable to adjust a length of the middle segment relative to a distal end of the proximal segment.

7. The robotic actuator of claim 6, wherein the first and third actuators are adjacent to each other.

8. The robotic actuator of claim 5, further comprising a fifth actuator that provides movement about a second axis of the end-effector with respect to the body of the instrument.

9. The robotic actuator of claim 7, further comprising a sixth actuator that provides movement about a third axis of the end-effector with respect to the body of the instrument.

10. The robotic actuator of claim 9, wherein the second, fifth and sixth actuators are adjacent to each other.

11. The robotic actuator of claim 9, wherein
the sixth actuator is coupled to a bevel gear, and
the second and fifth actuators are each coupled to a worm gear.

12. The robotic actuator of claim 5, further comprising mechanical element coupled between the second actuator and the end-effector, the mechanical element providing a speed reduction or force multiplication to the second actuator.

13. The robotic actuator of claim 12, wherein the mechanical element is a planetary gear.

14. The robotic actuator of claim 12, further comprising a pulley coupled between the mechanical element and the end-effector.

15. The robotic actuator of claim 14, further comprising a second mechanical element coupled between the pulley and the end-effector, the second mechanical element including a gear ratio that increases torque applied to the end-effector by the second actuator.

16. The robotic actuator of claim 5, wherein the third actuator is coupled to a threaded rod having a carrier engaged thereon, the carrier travelling along the threaded rod when an output of the third actuator rotates.

17. The robotic actuator of claim 16, wherein the third actuator includes one or more linear actuators.

18. The robotic actuator of claim 5, wherein the first actuator is coupled to a worm gear.

19. The robotic actuator of claim 18, wherein the worm gear is coupled to a gear.

20. The robotic actuator of claim 19, wherein the worm gear and the gear are coupled via an approximately 90 degree intersection.

21. The robotic actuator of claim 1, wherein the robotic actuator is generally cylindrical in shape.

22. The robotic actuator of claim 21, wherein a diameter of the cylinder is 21 mm or less.

23. The robotic actuator of claim 22, wherein a length of the cylinder is 200 mm or less.

24. The robotic actuator of claim 1, wherein the instrument assembly and the internal anchor are adapted to be coupled together before insertion into the body via the entrance port.

25. The robotic actuator of claim 24, wherein the instrument assembly is fixed to the internal anchor via the joint before insertion into the body via the entrance port.

26. The robotic actuator of claim 1, further comprising a circuit board.

27. The robotic actuator of claim 26, wherein the circuit board includes driver circuitry.

28. The robotic actuator of claim 26, wherein the circuit board includes a network interface.

29. The robotic actuator of claim 26, wherein the circuit board is flexible.

30. The robotic actuator of claim 26, wherein the circuit board is disposed adjacent to an inner wall of a housing of the instrument assembly.

\* \* \* \* \*